US009752935B2

(12) United States Patent
Marquardt et al.

(10) Patent No.: US 9,752,935 B2
(45) Date of Patent: Sep. 5, 2017

(54) PORTABLE ANALYTICAL EQUIPMENT

(71) Applicant: MarqMetrix, Inc., Seattle, WA (US)

(72) Inventors: Brian James Marquardt, Seattle, WA (US); John Scott Van Vuren, Seattle, WA (US)

(73) Assignee: MARQMETRIX, INC., Seattle, WA (US)

( * ) Notice: Subject to any disclaimer, the term of this patent is extended or adjusted under 35 U.S.C. 154(b) by 0 days.

(21) Appl. No.: 14/835,638

(22) Filed: Aug. 25, 2015

(65) Prior Publication Data

US 2016/0061663 A1    Mar. 3, 2016

Related U.S. Application Data

(60) Provisional application No. 62/043,983, filed on Aug. 29, 2014.

(51) Int. Cl.
| | |
|---|---|
| G08B 21/00 | (2006.01) |
| G01J 3/44 | (2006.01) |
| G01J 3/02 | (2006.01) |
| G01N 21/65 | (2006.01) |
| G08B 5/36 | (2006.01) |

(52) U.S. Cl.
CPC ............. *G01J 3/44* (2013.01); *G01J 3/027* (2013.01); *G01J 3/0218* (2013.01); *G01J 3/0264* (2013.01); *G01J 3/0272* (2013.01); *G01N 21/65* (2013.01); *G01N 2201/0221* (2013.01); *G08B 5/36* (2013.01)

(58) Field of Classification Search
CPC ........... G01J 3/44; G01J 3/0272; G01J 5/0846
USPC .. 340/540, 573.1, 539.12, 691.1, 691.6, 3.6, 340/10.1; 356/446, 6, 301, 952; 600/310
See application file for complete search history.

(56) References Cited

U.S. PATENT DOCUMENTS

| | | |
|---|---|---|
| 5,051,551 A | 9/1991 | Doyle |
| 5,186,263 A | 2/1993 | Kejr et al. |

(Continued)

OTHER PUBLICATIONS

International Search Report and Written Opinion mailed Feb. 11, 2016 for PCT Application No. PCT/US2015/063825, 9 pages.

(Continued)

*Primary Examiner* — Toan N Pham
(74) *Attorney, Agent, or Firm* — Amin, Turocy & Watson, LLP

(57) ABSTRACT

Portable analytical equipment, systems, methods, and techniques related thereto is disclosed. Portable analytical equipment can comprise a controller and a probe. The probe can interrogate a sample and receive a response to the interrogation. The controller can select and/or initiate an analysis related to interrogating the sample via the probe. The analysis can be selected from a portfolio of analyses stored on the controller. The controller can analyze the response to the interrogation based on reference data stored on the controller. The controller can determine an indication based on the analyzing the response for presentation via a low-power interface, which can comprise an LED or electrophoretic element. The controller can further be connected to an external device, e.g., a smartphone or remote PC, to present collected data and the analyzing of the response to the interrogation. The disclosed subject matter can be employed in hand-held analytical equipment, e.g., a hand-held Raman spectrometer.

28 Claims, 11 Drawing Sheets

(56) References Cited

U.S. PATENT DOCUMENTS

| | | | |
|---|---|---|---|
| 5,579,423 | A | 11/1996 | Tanaka et al. |
| 5,688,261 | A | 11/1997 | Amirkhanian et al. |
| 5,693,043 | A | 12/1997 | Kittrell et al. |
| 6,252,661 | B1 | 6/2001 | Hanna |
| 6,416,234 | B1 | 7/2002 | Wach et al. |
| 6,466,323 | B1 | 10/2002 | Anderson et al. |
| 6,831,745 | B2 | 12/2004 | Marquardt et al. |
| 6,977,729 | B2 | 12/2005 | Marquardt et al. |
| 7,599,075 | B2 | 10/2009 | Almogy et al. |
| 8,081,305 | B2 * | 12/2011 | Azimi ................ G01J 3/02 250/339.08 |
| 8,269,193 | B2 | 9/2012 | Christensen et al. |
| 8,373,140 | B2 | 2/2013 | Tokhtuev et al. |
| 9,222,875 | B2 * | 12/2015 | Egan ................ G01N 21/8483 |
| 2003/0001018 | A1 * | 1/2003 | Hussey ............ G06K 7/10851 235/472.01 |
| 2003/0076492 | A1 | 4/2003 | Bradbury et al. |
| 2004/0165183 | A1 | 8/2004 | Marquardt et al. |
| 2005/0248758 | A1 | 11/2005 | Carron et al. |
| 2006/0100743 | A1 | 5/2006 | Townsend et al. |
| 2006/0219558 | A1 | 10/2006 | Hafeman et al. |
| 2012/0092658 | A1 | 4/2012 | Azimi et al. |
| 2012/0140227 | A1 | 6/2012 | Willuweit et al. |
| 2012/0166211 | A1 | 6/2012 | Park et al. |
| 2013/0197119 | A1 | 8/2013 | Stapleton et al. |
| 2014/0004548 | A1 * | 1/2014 | Gordon ................ B01L 3/5029 435/21 |
| 2014/0046152 | A1 | 2/2014 | Bechtel et al. |
| 2014/0172315 | A1 * | 6/2014 | Vandersleen .... G01N 33/48785 702/19 |

OTHER PUBLICATIONS

Allred, et al. "Near-Infrared Raman Spectroscopy of Liquids and Solids with a Fiber-Optic Sampler, Diode Laser, and CCD Detector," Applied Spectroscopy 44(7): 1229-1231 (1990).

Angel, et al., "Some new uses for filtered fiber-optic Raman probes: In situ drug identification and in situ and remote Raman imaging," (1999) J. Raman Spectrosc, 30:795-805.

Aust, et al., "In situ analysis of a high-temperature cure reaction in real time using modulated fiber-optic FT-Raman spectroscopy," (1999) Applied Spectroscopy 53(6): 682-686. Retrieved on Dec. 22, 2015, 6 pages.

Cooney, et al., "Comparative study of some fiber-optic remote Raman probe designs. Part I: Model for liquids and transparent solids," (1996) Applied Spectroscopy 50(7): 836-848.

Cooney, et al., "Comparative study of some fiber-optic remote Raman probe designs. Part II: Tests of single-fiber, lensed, and flat and bevel-tip multi-fiber probes", (1996) Applied Spectroscopy 50(7): 849-860.

Cooney, et al., "Rare-earth-doped glass fiber for background rejection in remote fiber-optic Raman probes: theory and analysis of holmium-bearing glass," (1993) Applied Spectroscopy 47(10): 1683-1692.

Dai, et al., "Accurate procedure for determining the calibration curve of high-temperature molten salt systems via Raman spectroscopy," (1993) Applied Spectroscopy 47(8):1286-1288.

Dai, et al., "Temperature measurement by observation of the Raman spectrum of diamond," (1992) Applied Spectroscopy 44: 1229-1231.

Gilmore et al., "Quantitative detection of environmentally important dyes using diode laser/fiber-optic Raman spectroscopy", (1995) Applied Spectroscopy 49(4): 508-511.

Lin et al., "Feasibility of quantitative UV resonance Raman spectroscopy with a KrF excimer laser," (1987) Applied Spectroscopy 41(3) :422-427.

Ma et al., "Fiber Raman background study and its application in setting up optical fiber Raman probes," (1996) Applied Optics 35(15) 2527-2533.

Marquardt, et al., "Demonstration of a high precision optical probe for effective sampling of solids by Raman spectroscopy", (Oct. 2001) Proc. SPIE vol. 4469, p. 62-69, Raman Spectroscopy and Light Scattering Technologies in Materials Science, David L. Andrews; Ed.

McCreery, R.L. et al, "Fiber optic probe for remote Raman spectrometry," (1983) Anal. Chem. 55:146-148.

Zheng, et al., "Self-referencing Raman probes for quantitative analysis," (Apr. 2001) Applied Spectroscopy 55(4): 382-388, (2001). Retrieved on Dec. 22, 2015, 8 pages.

Schwab et al., "Remote, long-pathlength cell for high-sensitivity Raman spectroscopy," (1987) Applied Spectroscopy 41:126-130.

Schwab et al., "Normal and resonance Raman spectroelectrochemistry with fiber optic light collection" (1986) Anal. Chem. 58:2486-2492.

Trott, et al., "Angular resolved Raman scattering using fiber optic probes," (Nov. 1980) Rev. Sci. Instrum. 51 (11):1493-1496.

Wang, et al., "In situ monitoring of emulsion polymerization using fiber-optic Raman spectroscopy," (1992) Applied Spectroscopy 46(11): 1729-1731.

Xiao, et al, "Quantitative Raman spectral measurements using a diamond-coated all-silica fiber-optic probe," (1998) Applied Spectroscopy 52:626-628.

International Search Report and Written Opinion mailed Jan. 11, 2016 for PCT Application No. PCT/US2015/047012, 10 pages.

* cited by examiner

PORTABLE ANALYTICAL EQUIPMENT

RELATED APPLICATION

The subject patent application claims priority to U.S. Provisional Patent Application No. 62/043,983, filed Aug. 29, 2014, and entitled "Small, Robust, Handheld Raman Device for Analysis of Chemical and/or Biological Field Samples." The entirety of the aforementioned provisional application is hereby incorporated herein by reference.

TECHNICAL FIELD

The disclosed subject matter relates to portable analytical equipment, e.g., field deployable chemical analysis equipment. In some embodiments, the disclosed subject matter relates to hand-held optical analytical equipment, e.g., a hand-held Ramen spectrometer.

BACKGROUND

By way of brief background, conventional portable analytical equipment, e.g., field deployable chemical analysis equipment, is generally configured to provide detailed analytical information to a user in the field, e.g., via a graphical user interface comprising a display. In some conventional systems, the display can be similar to those found in modern smartphones, e.g., high resolution, touch-sensitive, etc., and can be a significant consumer of on-board power, e.g., a battery of the field deployable chemical analysis equipment. Moreover, conventional field deployable chemical analysis equipment can be configured for hyperaccurate or hypersensitive analytics that can demand highly specialized sensors, excitation sources, sample interfaces, etc., that correspondingly can result in larger, bulkier, less compact, less streamlined, etc., devices. Furthermore, this hyperaccurate or hypersensitive field deployable chemical analysis equipment can be exceedingly delicate. It can be commonly accepted that conventional field deployable chemical analysis equipment is not considered rugged, compact, highly portable, or power friendly, and thus can be associated with bulk increasing protective carrying cases, frequent recharging of a battery or use of a bulky external power supply, and increased training of user/operators.

DETAILED DESCRIPTION

Figure 1:
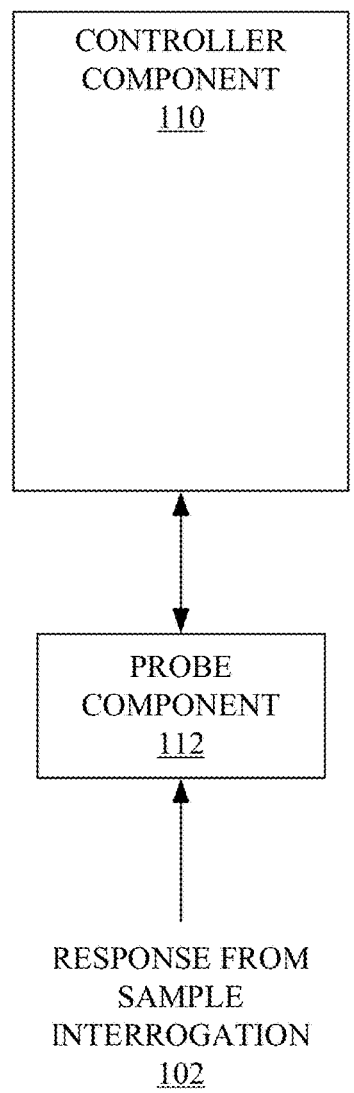
FIG. 1 is an illustration of an example system that facilitates portable analytical equipment in accordance with aspects of the subject disclosure.

The subject disclosure is now described with reference to the drawings, wherein like reference numerals are used to refer to like elements throughout. In the following description, for purposes of explanation, numerous specific details are set forth in order to provide a thorough understanding of the subject disclosure. It may be evident, however, that the subject disclosure may be practiced without these specific details. In other instances, well-known structures and devices are shown in block diagram form in order to facilitate describing the subject disclosure.

Conventional portable analytical equipment, e.g., conventional field deployable chemical analysis equipment, is generally configured to provide highly detailed analytical information to a user in the field, e.g., via a graphical user interface comprising a display. In some conventional systems, the display can be similar to those found in modern smartphones, e.g., high resolution, touch-sensitive, etc., and can be a significant drain of on-board power, e.g., a battery of the conventional field deployable chemical analysis equipment. Moreover, conventional field deployable chemical analysis equipment can be configured for hyperaccurate or hypersensitive analytics that can demand highly specialized sensors, excitation sources, sample interfaces, etc., that correspondingly can result in larger, bulkier, less compact, less streamlined, etc., devices. Furthermore, this hyperaccurate or hypersensitive field deployable chemical analysis equipment can be exceedingly delicate. Conventional field deployable chemical analysis equipment, while typically smaller than their non-portable lab installed counterparts, are still not generally construed to be rugged, compact, highly portable, or power friendly, and thus can be associated with bulk increasing protective carrying cases, frequent recharging of a battery or use of a bulky external power supply, and intensive training of user/operators.

Conventional portable analytical equipment can comprise a display, not unlike those found on modern smartphones, allow a user/operator to visualize the results of an analysis directly on the portable analytical equipment and to interact with the device to set parameters, etc. This display can increase the size of the device over portable analytical equipment that does not include an integrated display. Moreover, displays can consume significant power and, where portable analytical equipment is generally battery operated, can result in inclusion of a larger battery to support the display and/or shorter operational times of the portable analytical equipment between charging cycles, battery exchanges, etc.

Where conventional portable analytical equipment provides access to analysis results, these results can require user/operator training for interpretation in order to be meaningful. It makes little sense to present detailed analytical results to an untrained user/operator. Thusly, use of these conventional portable analytical equipment(s) can be relegated to trained personnel and be associated with increased cost of operation where training is needed to effectively deploy a trained user/operator with conventional portable analytical equipment.

In contrast to conventional portable analytical equipment, the presently disclosed subject matter can be related to portable analytical equipment that can dispense with an integrated display. This can allow the presently disclosed portable analytical equipment to employ a smaller form factor than conventional portable analytical equipment. Further, where an integrated display is not employed, operational life between charging/swapping a battery, for any given battery size, can be improved over conventional portable analytical equipment.

In some embodiments, an indicator can be employed to communicate more basic information to a user/operator, e.g., a green light can indicate a pass while a red light can indicate a fail for a condition. While this indicator can comprise much less detail than information that can be presented via a display associated with a conventional portable analytical equipment, the inherently simple nature of the indicator can provide other significant advantages over an integrated display.

In an aspect, an indicator can allow a user/operator to operate the device meaningfully with little training. In contrast to an integrated display, which can require a user to interpret the displayed analytical results, e.g., interpret a Raman spectrum, to comprehend a meaningful result form an analysis, an indicator can communicate more basic but meaningful information to a lesser trained operator. As an example, an indicator can comprise a series of light emitting diodes (LEDs) in a ramp pattern. Continuing the example, where a user is performing analyses testing for any one of a set of chemical warfare agents, such as chlorine gas, mustard gas, etc., illuminating more of the LED ramp pattern can indicate an increasing detected concentration of one of the target chemical agents being detected. While the specific chemical agent might not be communicated by the indicator in this particular example, the user can know that there is an increasing danger, a need for further testing, a need to escalate the response to the results to a more highly trained operator, etc., in response to the indicator progression. As is apparent in this particular example, nearly anyone with minimal training can execute the analysis of samples for chemical warfare agents with meaningful results. In contrast, while conventional portable analytical equipment could display more detailed information via an embedded display—even allowing a user to determine which of the chemical warfare agents is being detected in the above example—the user/operator would need significantly more training and expertise to operate the conventional portable analytical equipment and yield meaningful results.

In a further aspect, the use of indicators can consume less power than use of a display, allowing for fielded portable analytical equipment to either be smaller and/or operate for longer periods of time given equivalent batteries as would be in conventional portable analytical equipment. As an example, where a volcanologist carries their equipment quite literally up the side of a mountain to perform tests, reducing battery weight and device bulk can be an large advantage. In some embodiments, other "low-power indicators", meaning consuming less power than a typical embedded display, can include one or more multicolored LEDs, one or more single color LEDs, LEDs arranged in patterns, etc. However, LEDs, even though generally considered to be low power, can draw down a battery over extended periods of time, though not nearly as quickly as a liquid crystal display LCD, or similar display. Where even lower power consumption is desirable, some embodiments can comprise flag-type devices, e.g., mechanical flags that can be triggered but consume no other power, and/or technologies such as electrophoretics, more commonly known as e-ink or e-paper, to display indicators, graphics, symbols, letters, numbers, words, colors, etc., while drawing very minimal power in comparison to even an LED, more especially with bi-stable type 'pigments', etc., that can retain an image even with no external power.

In yet another aspect, where there is no display incorporated into the portable analytical equipment, the device can be more rugged, e.g., there is no screen to crack or break, meaning that the portable analytical equipment can require less bulky and weighty carrying cases than might be associated with conventional portable analytical equipment. Still further, in some embodiments of the presently disclosed subject matter, the portable analytical equipment can be made small enough to simply slip into a pocket and be rugged enough to be jostled in the pocket with keys, coins, etc. Also advantageously, not including a display in portable analytical equipment can reduce manufacturing, wholesale, and retail monetary costs as well, e.g., an LED and/or a wireless communication chip can be much lower cost than a touch sensitive color display.

In an embodiment, the presently disclosed portable analytical equipment can be communicatively coupled with another device, e.g., a laptop, smartphone, tablet, etc., to allow finer grain interaction with the portable analytical equipment. The other coupled device can provide a display for visualizing and/or interacting with analytical results that would be generally comparable to, or better than, conventional portable analytical equipment with an embedded display, e.g., coupling to a smartphone, which are becoming increasingly ubiquitous, can provide similar display area and resolution as conventional portable analytical equipment, and coupling to a tablet or laptop that might be carried by the user for myriad other reasons, can provide a display that is frequently larger and/or better resolution than displays comprised in conventional portable analytical equipment. Additionally, the ever increasing performance of these other devices, e.g., improved displays, battery life, processor speeds, memory volumes, etc., can allow the presently disclosed portable analytical equipment to remain highly relevant in contrast to conventional portable analytical equipment that are locked into the displays, processors, memory, and battery at their time of manufacture. As an example, where a smartphone five years from now is 10× faster, comprises a display that has 2× the resolution, and has a battery that is $\frac{1}{4}^{th}$ the weight and twice the power density of today's technology, the presently disclosed portable analytical equipment has a considerable advantage over conventional portable analytical equipment because it can couple to these improving technologies and leverage them to provide an improved user experience, e.g., the presently disclosed subject matter can age better than conventional portable analytical equipment.

In an aspect, wired and wireless connectivity can be employed, in addition to connection with an local external device, e.g., a laptop, smartphone, tablet, etc., for visualizing and interacting with the disclosed portable analytical equipment, for connection to remotely located devices and/or systems. In an embodiment, portable analytical equipment disclosed herein can connect to remotely located devices via a wired or wireless interface, e.g., cellular, Wi-Fi, Bluetooth, etc. This can facilitate communication of information via a communications infrastructure, e.g., cloud services, the World Wide Web, etc. In some embodiments, results of analytical interrogations can be communicated to these remote devices. This can include real-time, or near-real time, communication of interrogation results, as well as bundling sets of results and transmitting them together, e.g., burst transmission of analytical interrogation results. Moreover, in some embodiments, information can be communicated to the portable analytical equipment, e.g., control data, updating a portfolio of analyses or analysis thereof, running diagnostics, checking a status, triggering execution of an analysis, requesting data transmission, etc.

In some embodiments, portable analytical equipment disclosed herein can comprise a remote deployment interface component. This can facilitate remote deployment of device. The remote deployment interface can comprise a wired/ wireless communications interface, an external power interface, e.g., solar power, external battery, power over Ethernet (POE), mains power connectivity, etc., external memory and/or storage device interface, etc. The remote deployment interface can enable the disclosed portable analytical equipment to be readily remotely deployed. As an example, monitoring dissolved gasses in a lake for the presence of high levels of methane or sulfur compounds can be facilitated via the remote deployment interface allowing connectivity to a solar power source and an wireless transmitter such that the portable analytical equipment can be deployed lakeside and left to perform an analysis form the portfolio of analyses while being wirelessly connected, e.g., to report when high levels are detected, and powered by the sun.

In some embodiments of the presently disclosed subject matter, portable analytical equipment can further comprise a memory or storage device that can enable access to a portfolio of analyses. An analysis can be defined and stored in the portfolio to allow the analysis to be selected from the portfolio when the portable analytical equipment is deployed. As an example, where portable analytical equipment has three programmable buttons for selecting an analysis, each of these buttons can be assigned an analysis stored in the portfolio. As another example, where a portable analytical equipment is coupled to a smartphone, the smartphone can enable selection of any analysis stored in the portfolio. The stored analysis can comprise parameters and settings. As examples, an analysis can trigger iteratively on a time interval, can average a determined number of sample runs, can employ designated excitation sources, e.g., in an optical analysis different wavelengths, different power densities, different focal conditions, etc., can be determined, determined alert or indicator parameters, or nearly any other parameter or setting associated with an analysis by portable analytical equipment can be included in a stored analysis. As such, the portfolio of analyses can enable different analyses to be readily selected and employed. Moreover, where the portfolio is stored at the portable analytical equipment, these analyses can be selected with, or without, wired or wireless connectivity. As an example, a plurality of water contaminant analyses can be performed at a reservoir, even where the reservoir is so remote that the portable analytical equipment may not be able to establish a data connection to the outside world.

Moreover, in some embodiments, analysis can be performed at the portable analytical equipment with, or without, a wired or wireless connection by storing reference analysis data in a memory or storage device of the portable analytical equipment. As an example, Raman spectra for known chemical compounds, e.g., a Raman spectral library, can be stored on a memory of a portable analytical equipment. The results of a Raman interrogation of a sample can be compared to the Raman spectral library to facilitate analysis of the results of the Raman interrogation. In an aspect, stored reference analytical data can tailored to particular application, e.g., the libraries can be use specific, for example, a library of reference analytical data for a portable analytical equipment deployed in a food processing plant can be significantly different from a library on a portable analytical equipment deployed in fission reactor environment.

In some embodiments, the disclosed portable analytical equipment can employ a probe component coupled to a controller component. The probe component can be fixed to the controller component, flexibly attached to the controller component, removable attached to the controller component, retractably attached to the controller component, etc. As an example, the probe component can comprise a Ball-Probe™ (MarqMetrix Inc., Seattle, Wash.) for Raman immersion testing. The probe component can comprise other technologies, e.g., a infrared (IR) probe, an resistance probe, a conductivity probe, a pH probe, a biomarker probe, etc., without departing form the scope of the presently disclosed subject matter as will be appreciated by one of skill in the relevant arts.

To the accomplishment of the foregoing and related ends, the disclosed subject matter, then, comprises one or more of the features hereinafter more fully described. The following description and the annexed drawings set forth in detail certain illustrative aspects of the subject matter. However, these aspects are indicative of but a few of the various ways in which the principles of the subject matter can be employed. Other aspects, advantages and novel features of the disclosed subject matter will become apparent from the following detailed description when considered in conjunction with the provided drawings.

FIG. 1 is an illustration of a system 100, which facilitates portable analytical equipment in accordance with aspects of the subject disclosure. System 100 can comprise controller component 110. Controller component 110 can control execution of an analytical interrogation. Controller component 110 can further control execution of an analysis related to the analytical interrogation. Additionally, controller component 110 can control interactions with a user/operator, e.g., via a user interface, via other devices, etc. In an aspect, controller component 110 can enable presentation of an indicator related to a result of analysis, e.g., via a low-power user interface, via other devices coupled to controller component 110, via other devices located remotely and coupled to controller component 110 via network components such as a Wi-Fi access point, etc.

Controller component 110 can be communicatively coupled to probe component 112. In some embodiments, probe component can be part of, or integrated with, controller component 110, e.g., the probe can be mechanically attached to a housing that houses controller component 110 to form a portable analytical equipment device. In an aspect, probe component 112 can be retractable, in whole or in part, allowing devices comprising probe component 112 and controller component 110 to be more compact in a probe-retracted configuration than in a probe-extended configuration. As an example, a hand held portable analytical equipment device can house probe component 112 in a retracted position such that probe component 112 can be extended, e.g., in a stiletto knife manner, rotated or folded out into an extend position, detached from the retracted position and reattached in an extended position, etc.

In other embodiments, probe component 112 can be flexibly connected to controller component 110. In an aspect, probe component 112 can comprise a 'goose-neck' type flexible portion, a pivot portion, a rotatable portion, etc., allowing the disposition of probe component 112 relative to controller component 110 to be changed. As an example, probe component 112 can comprise a flexible portion, such as an elastomeric portion, etc., to enable probe component 112 to be employed in different positions relative to controller portion 110, such as deflecting sufficiently to allow probe component 112 to interrogate a sample in an area that would restrict use of a portable analytical equipment device that did not comprise probe component 112 having a flexible portion. This flexibility can allow portable analytical equipment to be employed in environments such as crowded process lines, deploying probe component 112 into fissures or holes in rocky areas not large enough to insert a rigidly attached probe component 112, into sample areas in awkward locations for more comfortable user operation, such as vehicle exhausts, etc., and the like.

In further embodiments, probe component 112 can be coupled to controller component 110 via a conductor and/or a fiber optic. This can allow probe component 112 to be deployable in a manner that is nearly unrelated to the deployment of controller component 110. As an example, probe component 112 can be connected to controller component 110 via a length of fiber optic cable allowing probe component 112 to be lowered into a deep hole, such as a well, fissure in a rock, a crevasse, into a layer of ocean or lake water of interest, into an oil tank, etc., and while remaining controllable via controller component 110.

In an embodiment, probe component 112 can comprise a BallProbe™ (MarqMetrix Inc., Seattle, Wash.). Ball Probe™ can enable Raman spectrometry of an environment. In an aspect, the BallProbe™ can allow for in-situ Raman spectrometry via probe component 112. The BallProbe™ can be controlled by controller component 110 via the communicative coupling between controller component 110 and probe component 112. An example portable analytical equipment device comprising a BallProbe™ can perform Raman spectrometry by dipping or inserting the BallProbe™ into a sample environment and initiating an analytical interrogation of said sample environment. The analytical interrogation can excite atomic bonds of molecules in the sample environment such that a Raman spectrum can be captured, e.g., response form sample interrogation 102. The Raman spectrum can then be analyzed by controller component 110. The analysis of the Raman spectrum can be based on reference Raman spectra stored at controller component 110, e.g., on a memory or storage device, and in accord to with an analysis, such as an analysis stored in a portfolio of analyses that can also be stored at controller component 110, e.g., on a memory or storage device. Of note, the terms 'spectrometry' and 'spectroscopy' are frequently used interchangeably in the art, though they can have slightly different connotations. The term 'spectrometry' is used in this disclosure in relation to the capture, analysis, and generation of results based on spectral information elicited via interrogation of a sample, as 'spectrometry' is believed to be the more correct term in this regard. However, the term 'spectrometry' is to be treated as inclusive of the common connotation of the term 'spectroscopy' as used by those of skill in the related art, unless otherwise explicitly indicated as having a narrower or different meaning in this disclosure.

In an aspect, controller component 110 can receive an analysis and can then institute the analysis via a portable analytical equipment device comprising controller component 110. In some embodiments, controller component 110 can comprise a memory or storage device that can have stored thereon one or more analysis. In an aspect, the memory or storage device can comprise a portfolio of analyses comprising the one or more analysis. An analysis can be defined and stored in the portfolio to allow the analysis to be selected from the portfolio when a portable analytical equipment device comprising controller component 110 is deployed. As an example, where a portable analytical equipment device has a plurality of programmable buttons related to selecting an analysis, each of these buttons can be assigned an analysis stored in the portfolio to enable rapid selection of relevant analyses from the portfolio. As another example, where a portable analytical equipment device is coupled to a tablet computer, the tablet computer can enable selection of any analysis stored in the portfolio. The stored analysis can comprise parameters and settings. As examples, an analysis can trigger iteratively on a time interval, can average a determined number of sample runs, can employ designated excitation sources, e.g., in an optical analysis different wavelengths, different power densities, different focal conditions, etc., can be determined, determined alert or indicator parameters, or nearly any other parameter or setting associated with an analysis by a portable analytical equipment device comprising controller component 110 can be included in a stored analysis. As such, the portfolio of analyses can enable different analyses to be readily selected and employed. Moreover, where the portfolio is stored at the portable analytical equipment, these analyses can be selected with, or without, wired or wireless connectivity. In embodiments where the portfolio is stored on an external storage device, e.g., a flash drive that can be plugged into, e.g., connected to, controller component 110, an analysis can be selected therefrom. Further, the removable storage device can allow rapid selection of another portfolio of analyses by simply swapping the removable storage device for another having stored thereon a different portfolio of analyses. In additional embodiments, the portfolio of analyses can be stored on another device, e.g., a smartphone, laptop, tablet computer, etc., or a remotely located device, server, remotely located computer, etc., allowing execution of an analysis from nearly any source. Of course, where the portfolio is located other than at controller component 110, some communicative coupling between the portfolio and controller component 110 can be employed to allow the analysis to be 'loaded' into controller component 110 for execution. In contrast, a portfolio in a memory of storage device of controller component 110 can operate without such a communicative coupling to external resources, e.g., no connection to a remote server is needed to perform the analysis when the analysis is selected from a portfolio stored on a memory of controller component 110.

In another aspect, controller component 110 can perform an analysis in accord with a received analysis, e.g., from a portfolio of analyses, based on reference analysis data. Reference analysis data can be received by controller component 110. In an aspect, reference analysis data can be stored on a memory or storage device of controller component 110. As an example, Raman spectra for known chemical compounds, e.g., a Raman spectral library, can be stored on a memory of a portable analytical equipment device comprising controller component 110. The results of a Raman interrogation of a sample can be compared to the Raman spectral library to facilitate analysis of the results of the Raman interrogation. In an aspect, stored reference analytical data can be tailored to particular application, e.g., the libraries can be industry specific, for example, a library of reference analytical data for a portable analytical equipment deployed in the food processing industry can be significantly different from a library for the nuclear submarine industry or a library for the oil refining industry.

In an embodiment, controller component 110 can initiate an analysis in response to a received trigger. In an aspect, the trigger can be caused by an operator, e.g., a user presses a button, shakes the device, etc. In another aspect, the trigger can be associated with a received analysis. The received analysis can designate a trigger value, such as timed intervals, time of day, scheduled times, analysis on a detected change in a sampling environment, etc. As an example, controller component 110 can receive an analysis that instructs that an analysis be initiated every ten minutes or where a change in the sample environment is detected, and if a change in the sample environment is detected, then an analysis should be conducted once a minute for ten minutes. As another example, controller component 110 can receive an analysis that instructs that an analysis be initiated when an external temperature transitions a threshold temperature, such as when the temperature drops below freezing, when the temperature goes above 160 C., etc. In a further aspect, controller component 110 can receive an analysis that instructs that limits initiation of an analysis to certain conditions, e.g., when temperature is between two set points, when a battery is above a threshold charge level, etc. As an example, controller component 110 can receive an analysis that instructs that an analysis be initiated when a change in the sample environment is detected but only if the sample environment temperature is between 90 C. and 110 C., etc.

In an embodiment, controller component can enable operation of portable analytical equipment that does not comprise an embedded LCD-type display, e.g., comparable to a modern smartphone display. By dispensing with an integrated display, controller component 110 can be employed in a smaller form factor than conventional portable analytical equipment. Further, where an integrated display is not employed, operational life between charging/swapping a battery can be improved over conventional portable analytical equipment. Moreover, in some embodiments, controller component 110 can support operation of an indicator that can be employed to communicate relatively basic information to a user/operator, e.g., a green light can indicate a pass/safe/undetected while a red light can indicate a fail/danger/detected. While an indicator can comprise much less detailed information than can typically be presented via an LCD-type display, the inherently simple nature of the indicator can be advantageous over integrated displays.

In an aspect, controller component 110 can employ an indicator to allow a user/operator to operate the device meaningfully with little training. In contrast to an integrated LCD display, which can need skilled interpretation, an indicator can communicate more basic, but still meaningful information, to an operator, even those with low skill levels. As an example, controller component 110 can control a series of LEDs as an indicator. Where a user is performing analyses testing, illuminating more of the LEDs can indicate a target molecule is detected. As such, detection can be communicated without needing to train the operator to interpret a displayed result, such as a displayed optical spectrum. The user can therefore be aware of a positive detection result and can then determine any need for further testing, an need to have results reviewed by a more highly trained operator, etc.

In a further aspect, controller component 110 use of indicators can consume less power than typically associated with a conventional LCD-type display, allowing for fielded portable analytical equipment to either be smaller and/or operate for longer periods of time. In some embodiments, other "low-power" indicators, meaning any indicator consuming less power than a typical embedded LCD-type display, can include one or more multicolored LEDs, one or more single color LEDs, LEDs arranged in patterns, etc. However, LEDs, even though generally considered to be low power, can still drain a battery over extended periods of time, though not nearly as quickly as an LCD-type display. Where even lower power consumption can be desirable, some embodiments can comprise controller component 110 control of flag-type devices, e.g., mechanical flags that can be triggered but otherwise consume no other power; electrophoretics, more commonly known as e-ink or e-paper, to display indicators, graphics, symbols, letters, numbers, words, colors, etc., while drawing very minimal power in comparison to even an LED, more especially with bi-stable type 'pigments', etc., that can retain an image even with no external power; etc.

In yet another aspect, where there is no display incorporated into the portable analytical equipment, the device can be more rugged, e.g., there is no screen to crack or break, meaning that the portable analytical equipment can be deployed without bulky and weighty protective cases than might be associated with conventional portable analytical equipment. Still further, in some embodiments of the presently disclosed subject matter, the portable analytical equipment comprising controller component 110 and probe component 112 can be made small enough to simply slip into a pocket, pouch on a backpack, glovebox in a vehicle, etc. Also advantageously, separating a conventional LCD-type display from portable analytical equipment can lower manufacturing, wholesale, and retail monetary costs as well.

In an embodiment, controller component 110, of the presently disclosed portable analytical equipment, can be communicatively coupled with another device (not illustrated), e.g., a laptop, smartphone, tablet, etc., to allow interaction with controller component 110 via the other device. The other coupled device can provide a display for visualizing and/or interacting with analytical results that would be generally comparable to, or better than, conventional portable analytical equipment with an embedded display, e.g., coupling to a smartphone, that are increasingly ubiquitous, can provide similar display area and resolution to a conventional portable analytical equipment and coupling to a tablet or laptop that might be carried by the user for myriad other reasons, can provide a display that is frequently larger and/or better resolution that displays comprised in conventional portable analytical equipment. Additionally, the ever increasing performance of these other devices, e.g., improved displays, battery life, processor speeds, memory volumes, etc., can allow the presently disclosed portable analytical equipment to remain highly relevant in contrast to conventional portable analytical equipment that are locked into the displays, processors, memory, and battery at their time of manufacture. This can be a considerable advantage over conventional portable analytical equipment because these improving technologies can then be leveraged to provide an improved user experience as they come to market.

In a further aspect, controller component 110 can comprise wired and wireless connectivity. This can enable connection with a local external device, e.g., a laptop, smartphone, tablet, etc., as well as remotely located devices, for visualizing and interacting with the controller component 110. In an embodiment, controller component 110 can connect to remotely located devices via a wired or wireless interface, e.g., cellular, Wi-Fi, Bluetooth, etc. This can facilitate communication of information via a communications infrastructure, e.g., cloud services, the World Wide Web, etc. In some embodiments, results of analytical interrogations can be communicated to these remote devices by controller component 110. This can include real-time, or near-real time, communication of interrogation results, as well as bundling sets of results and transmitting them together, e.g., burst transmission of analytical interrogation results. Moreover, in some embodiments, information can be communicated to controller component 110, e.g., control data, updating a portfolio of analyses or analysis thereof, running diagnostics, checking a status, triggering execution of an analysis, requesting data transmission, etc., can be sent to controller component 110 via a wired or wireless interface of controller component 110.

In some embodiments, controller component 110 can comprise a remote deployment interface component (not illustrated). This can facilitate remote deployment of a device comprising controller component 110. The remote deployment interface can comprise a wired/wireless communications interface, an external power interface, e.g., solar power, external battery, power over Ethernet (POE), mains power connectivity, etc., external memory and/or storage device interface, etc. The remote deployment interface can enable a portable analytical equipment comprising controller component 110 to be readily remotely deployed. As an example, monitoring chlorine levels in a city water system can be facilitated via the remote deployment interface where a network connection and power can be provided via an Ethernet cable connected to the remote deployment interface.

In some embodiments, controller component 110 and probe component 112 can be packaged in a hand held device. This small form factor can be facilitated by employing indicators in lieu of incorporating a conventional LCD-type display in to the hand held device. This small form factor can further be facilitated by employing a retractable probe component 112, such as a retractable BallProbe™. This small form factor can also be facilitated by employing a smaller battery than might be needed in a conventional device due to power consumption by a conventional LCD-type display. Of note, small, low cost, rugged, and capable portable analytical equipment can be highly desired in many fields using analytical equipment, more especially where training of operators can be substantially reduced. The presently disclosed subject matter, such as system 100, can facilitate these types of portable analytical equipment.

Figure 2:
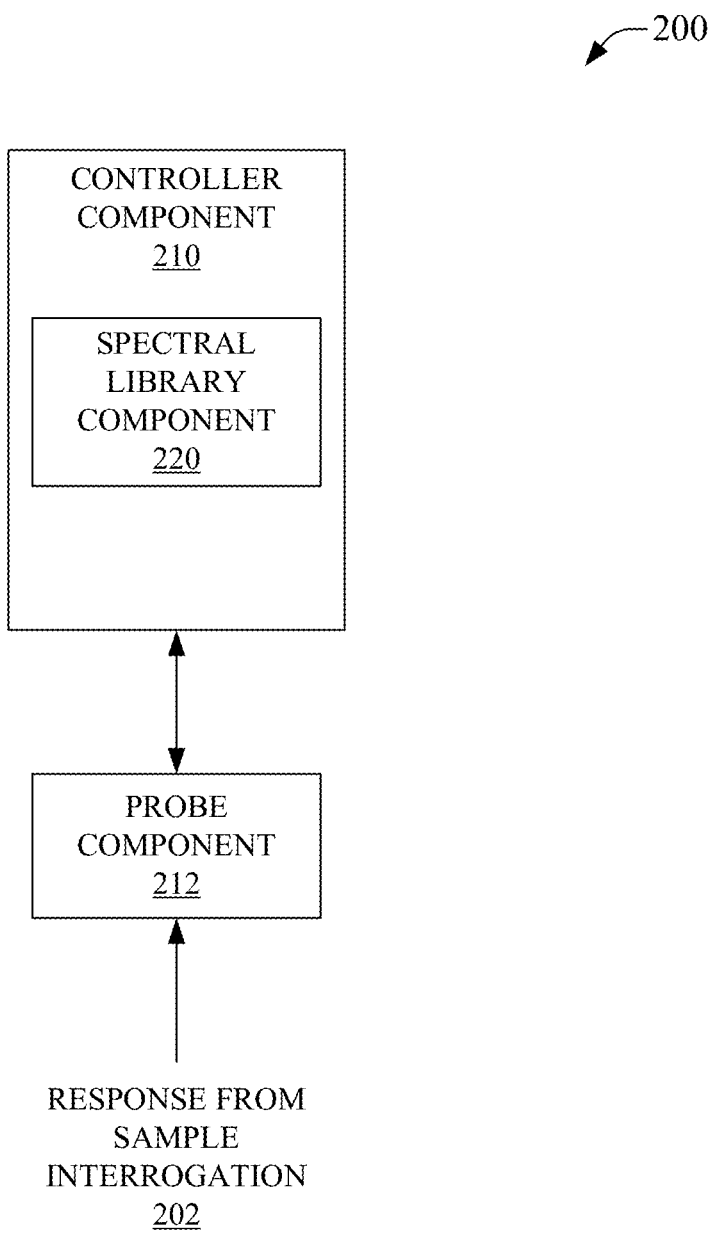
FIG. 2 is a depiction of an example system that facilitates portable spectral analysis in accordance with aspects of the subject disclosure.

FIG. 2 is a depiction of a system 200 that can facilitate portable spectral analysis in accordance with aspects of the subject disclosure. System 200 can comprise controller component 210. Controller component 210 can control execution of an analytical interrogation, e.g., via probe component 212. Controller component 210 can further control execution of an analysis related to the analytical interrogation, e.g., in response to receiving response from sample interrogation 202 via probe component 212. Additionally, controller component 210 can control interactions with a user/operator, e.g., via a user interface, via other devices, etc. In an aspect, controller component 210 can enable presentation of an indicator related to a result of analysis, e.g., via a low-power user interface, via other devices coupled to controller component 210, via other devices located remotely and coupled to controller component 210 via network components such as a Wi-Fi access point, etc.

Controller component 210 can be communicatively coupled to probe component 212. In some embodiments, probe component can be part of, or integrated with, controller component 210, e.g., the probe can be mechanically attached to a housing that houses controller component 210 to form a portable analytical equipment device. In an aspect, probe component 212 can be retractable, in whole or in part, allowing devices comprising probe component 212 and controller component 210 to be more compact in a probe-retracted configuration than in a probe-extended configuration. As an example, a hand held portable analytical equipment device can house probe component 212 in a retracted position such that probe component 212 can be extended, e.g., in a stiletto knife manner, rotated or folded out into an extend position, detached from the retracted position and reattached in an extended position, etc. In other embodiments, probe component 212 can be flexibly connected to controller component 210. In an aspect, probe component 212 can comprise a 'goose-neck' type flexible portion, a pivot portion, a rotatable portion, etc., allowing the disposition of probe component 212 relative to controller component 210 to be changed. In further embodiments, probe component 212 can be coupled to controller component 210 via a conductor and/or a fiber optic. This can allow probe component 212 to be deployable in a manner that is nearly unrelated to the deployment of controller component 210. In an embodiment, probe component 212 can comprise a BallProbe™ (MarqMetrix Inc., Seattle, Wash.). Ball Probe™ can enable Raman spectrometry of an environment. In an aspect, the BallProbe™ can allow for in-situ Raman spectrometry via probe component 212. The BallProbe™ can be controlled by controller component 210 via the communicative coupling between controller component 210 and probe component 212.

In an aspect, controller component 210 can receive an analysis and can then institute the analysis via a portable analytical equipment device comprising controller component 210. In some embodiments, controller component 210 can comprise a memory or storage device that can have stored thereon one or more analysis. In an aspect, the memory or storage device can comprise a portfolio of analyses comprising the one or more analysis. An analysis can be defined and stored in the portfolio to allow the analysis to be selected from the portfolio when a portable analytical equipment device comprising controller component 210 is deployed. The stored analysis can comprise parameters and settings. As such, the portfolio of analyses can enable different analyses to be readily selected and employed. Moreover, where the portfolio is stored at the portable analytical equipment, these analyses can be selected with, or without, wired or wireless connectivity. In embodiments where the portfolio is stored on an external storage device, e.g., a flash drive that can be plugged into, e.g., connected to, controller component 210, an analysis can be selected therefrom. Further, the removable storage device can allow rapid selection of another portfolio of analyses by simply swapping the removable storage device for another having stored thereon a different portfolio of analyses. In additional embodiments, the portfolio of analyses can be stored on another device, e.g., a smartphone, laptop, tablet computer, etc., or a remotely located device, server, remotely located computer, etc., allowing execution of an analysis from nearly any source. Where the portfolio is located other than at controller component 210, a communicative coupling between the portfolio and controller component 210 can be employed to allow the analysis to be 'loaded' into controller component 210 for execution. In contrast, a portfolio in a memory of storage device of controller component 210 can operate without such a communicative coupling to external resources, e.g., no connection to a remote server is needed to perform the analysis when the analysis is selected from a portfolio stored on a memory of controller component 210.

In another aspect, controller component 210 can comprise spectral library component 220 to enable performing an analysis in accord with a received analysis, e.g., from a portfolio of analyses, based on reference spectral analysis data. Reference spectral analysis data can be received by controller component 210. In an aspect, reference spectral analysis data can be stored on a memory or storage device of controller component 210, e.g., spectral library component 220. As an example, Raman spectra for known chemical compounds, e.g., a Raman spectral library, can be stored by spectral library component 220 on a memory of a portable analytical equipment device comprising controller component 210. The results of a Raman interrogation of a sample can be compared to the Raman spectral library to facilitate analysis of the results of the Raman interrogation. In an aspect, stored reference spectral analytical data can tailored to particular application, e.g., the libraries can be industry specific, for example, a library of reference spectral analytical data for a portable analytical equipment deployed in a refinery processing industry can be significantly different from a library for the fertilizer industry or a library for the geological industry. In some embodiments, reference spectral analysis data can be received by controller component 210 from other local or remotely located memory, e.g., a local UE such as UE 440, from a remote server, from a cloud-based spectral library component, etc.

In an embodiment, controller component 210 can initiate an analysis in response to a received trigger. In an aspect, the trigger can be caused by an operator, e.g., a user presses a button, shakes the device, etc. In another aspect, the trigger can be associated with a received analysis. The received analysis can designate a trigger value, such as timed intervals, time of day, scheduled times, analysis on a detected change in a sampling environment, etc. In a further aspect, controller component 210 can receive an analysis that limits initiation of an analysis to certain conditions, e.g., when temperature is between two set points, when a battery is above a threshold charge level, etc.

In an embodiment, controller component can enable operation of portable analytical equipment that does not comprise an embedded LCD-type display, e.g., comparable to a modern smartphone display. By dispensing with an integrated display, controller component 210 can be employed in a smaller form factor than conventional portable analytical equipment. Further, where an integrated display is not employed, operational life between charging/swapping a battery can be improved over conventional portable analytical equipment. Moreover, in some embodiments, controller component 210 can support operation of an indicator that can be employed to communicate comparatively basic information to a user/operator, e.g., a green light can indicate a pass/safe/undetected while a red light can indicate a fail/danger/detected. While an indicator can comprise much less detailed information than can typically be presented via an LCD-type display, the inherently simple nature of the indicator can be advantageous over integrated displays.

In an aspect, controller component 210 can employ an indicator to allow a user/operator to operate the device meaningfully with little training. In contrast to an integrated LCD display, which can need skilled interpretation, an indicator can communicate more basic, but still meaningful information, to an operator, even those with low skill levels. As such, detection can be communicated without needing to train the operator to interpret a displayed result, such as a displayed optical spectrum. The user can therefore be aware of detection result and can then determine any need for further testing, a need to have results reviewed by a more highly trained operator, etc.

In a further aspect, controller component 210 use of indicators can consume less power than typically associated with a conventional LCD-type display, allowing for fielded portable analytical equipment to either be smaller and/or operate for longer periods of time. In some embodiments, other "low-power" indicators, meaning any indicator consuming less power than a typical embedded LCD-type display, can include one or more multicolored LEDs, one or more single color LEDs, LEDs arranged in patterns, etc. However, LEDs, even though generally considered to be low power, can still drain a battery over extended periods of time, though not nearly as quickly as an LCD-type display. Where even lower power consumption can be desirable, some embodiments can comprise controller component 210 control of flag-type devices, e.g., mechanical flags, electrophoretics, etc.

In yet another aspect, where there is no display incorporated into the portable analytical equipment, the device can be more rugged, e.g., there is no screen to crack or break, meaning that the portable analytical equipment can be deployed without bulky and weighty protective cases than might be associated with conventional portable analytical equipment. Still further, in some embodiments of the presently disclosed subject matter, the portable analytical equipment comprising controller component 210 and probe component 212 can be made small enough to simply slip into a pocket, pouch on a backpack, glovebox, etc. Also advantageously, separating a conventional LCD-type display from portable analytical equipment can lower manufacturing, wholesale, and retail monetary costs as well.

In an embodiment, controller component 210 can be communicatively coupled with another device (not illustrated), e.g., a laptop, smartphone, tablet, etc., to allow interaction with controller component 210 via the other device. The other coupled device can provide a display for visualizing and/or interacting with analytical results that would be generally comparable to, or better than, conventional portable analytical equipment with an embedded display, e.g., coupling to a smartphone can provide similar display area and resolution as conventional portable analytical equipment, and coupling to a tablet or laptop can provide a display that is frequently larger and/or better resolution that displays comprised in conventional portable analytical equipment. Additionally, the increasing performance of these other devices can allow the presently disclosed portable analytical equipment to remain highly relevant where external devices continue to evolve. This can be a considerable advantage over conventional portable analytical equipment because these improving technologies can then be leveraged to provide an improved user experience as they come to market.

In a further aspect, controller component 210 can comprise wired and wireless connectivity. This can enable connection with a local external device, e.g., a laptop, smartphone, tablet, etc., as well as remotely located devices, for visualizing and interacting with the controller component 210. In an embodiment, controller component 210 can connect to remotely located devices via a wired or wireless interface, e.g., cellular, Wi-Fi, Bluetooth, etc. This can facilitate communication of information via a communications infrastructure, intranet, internet, WAN, LAN, ad-hoc networks, etc. In some embodiments, results of analytical interrogations can be communicated to these remote devices by controller component 210. This can include real-time, or near-real time, communication of interrogation results, as well as bundling sets of results and transmitting them together, e.g., burst transmission of analytical interrogation results. Moreover, in some embodiments, information can be communicated to controller component 210, e.g., control data, updating an a portfolio of analyses or analysis thereof, running diagnostics, checking a status, triggering execution of an analysis, requesting data transmission, etc., can be sent to controller component 210 via a wired or wireless interface of controller component 210.

In some embodiments, controller component 210 can comprise a remote deployment interface component. This can facilitate remote deployment of a device comprising controller component 210. The remote deployment interface can comprise a wired/wireless communications interface, an external power interface, e.g., solar power, external battery, power over Ethernet (POE), mains power connectivity, etc., external memory and/or storage device interface, etc. The remote deployment interface can enable portable analytical equipment comprising controller component 210 to be readily remotely deployed.

In some embodiments, controller component 210 and probe component 212 can be packaged in a hand held device. This small form factor can be facilitated by employing indicators in lieu of incorporating a conventional LCD-type display in to the hand held device. This small form factor can further be facilitated by employing a retractable probe component 212, such as a retractable BallProbe™. This small form factor can also be facilitated by employing a smaller battery than might be needed in a conventional device due to power consumption by a conventional LCD-type display. Of note, small, low cost, rugged, and capable portable analytical equipment can be highly desired in many fields using analytical equipment, more especially where training of operators can be substantially reduced. The presently disclosed subject matter, such as system 200, can facilitate these types of portable analytical equipment.

Figure 3:
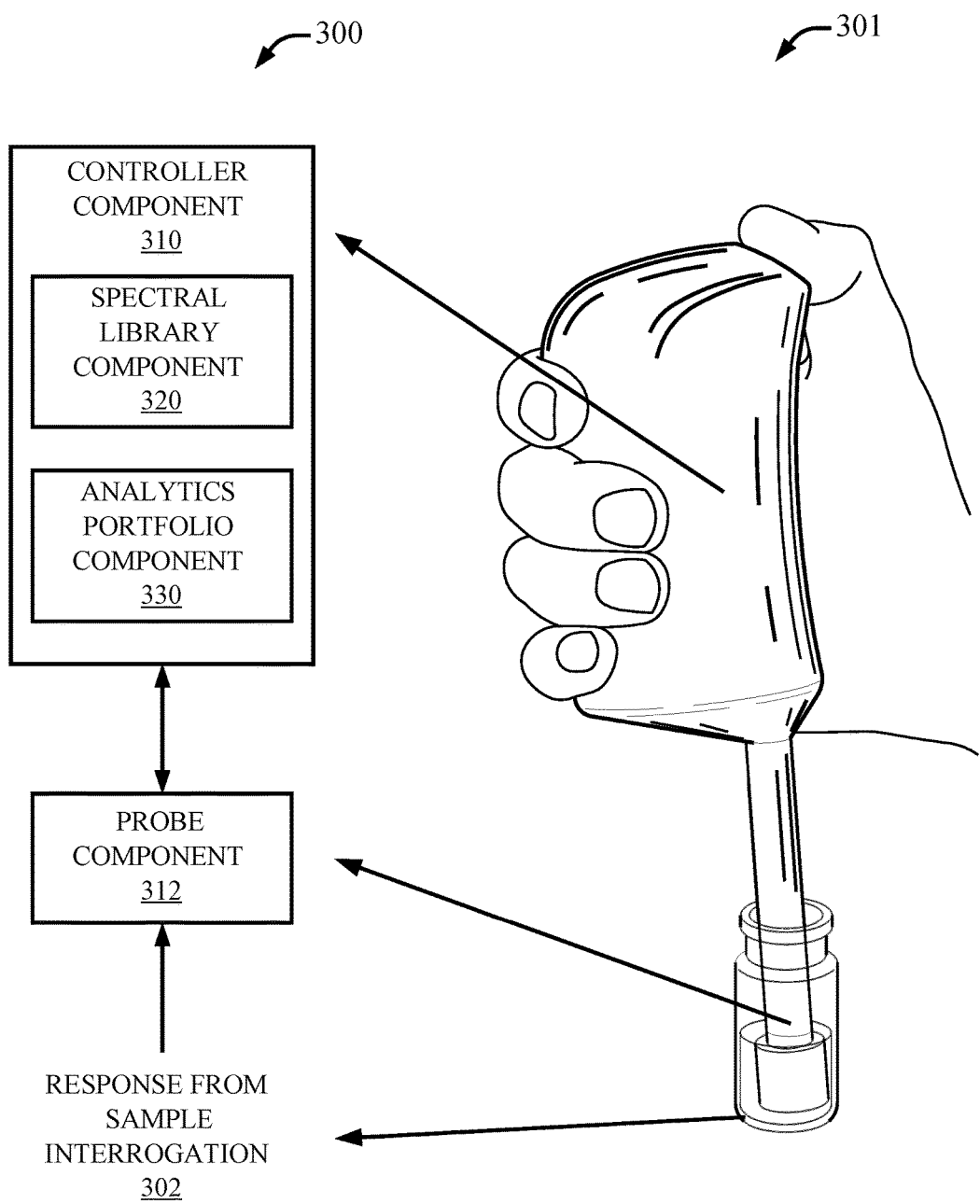
FIG. 3 illustrates an example system that facilitates portable spectral analysis via a portfolio of locally stored analytical procedures in accordance with aspects of the subject disclosure.

FIG. 3 illustrates a system 300 that facilitates portable spectral analysis via a portfolio of locally stored analytical procedures in accordance with aspects of the subject disclosure. System 300 can comprise controller component 310. Controller component 310 can control execution of an analytical interrogation, e.g., via probe component 312. Controller component 310 can further control execution of an analysis related to the analytical interrogation, e.g., in response to receiving response from sample interrogation 302 via probe component 312. Additionally, controller component 310 can control interactions with a user/operator, e.g., via a user interface, via other devices, etc. In an aspect, controller component 310 can enable presentation of an indicator related to a result of analysis, e.g., via a low-power user interface, via other devices coupled to controller component 310, via other devices located remotely and coupled to controller component 310 via network components such as a Wi-Fi access point, etc. Further illustrated is an image 301 of an example portable analytical equipment device developed by MarqMetrix Inc. of Seattle, Wash., with arrows corresponding to the several components disclosed in relation to system 300. This illustrates example locations of a controller component 310, probe component 312, and response from sample interrogation 302, in regards to the example portable analytical equipment device depicted in image 301.

Controller component 310 can be communicatively coupled to probe component 312. In some embodiments, probe component can be part of, or integrated with, controller component 310, e.g., the probe can be mechanically attached to a housing that houses controller component 310 to form a portable analytical equipment device, see for example the example portable analytical equipment device depicted in image 301. In an aspect, probe component 312 can be retractable, in whole or in part, allowing devices comprising probe component 312 and controller component 310 to be more compact in a probe-retracted configuration than in a probe-extended configuration. As an example, a hand held portable analytical equipment device can house probe component 312 in a retracted position such that probe component 312 can be extended, e.g., in a stiletto knife manner, rotated or folded out into an extend position, detached from the retracted position and reattached in an extended position, etc. In other embodiments, probe component 312 can be flexibly connected to controller component 310. In an aspect, probe component 312 can comprise a 'goose-neck' type flexible portion, a pivot portion, a rotatable portion, etc., allowing the disposition of probe component 312 relative to controller component 310 to be adapted in the field. In further embodiments, probe component 312 can be coupled to controller component 310 via a conductor and/or a fiber optic. This can allow probe component 312 to be deployable in a manner that is nearly unrelated to the deployment of controller component 310. In an embodiment, probe component 312 can comprise a BallProbe™ (MarqMetrix Inc., Seattle, Wash.). Ball Probe™ can enable Raman spectrometry of an environment. In an aspect, the BallProbe™ can allow for in-situ Raman spectrometry via probe component 312. The BallProbe™ can be controlled by controller component 310 via the communicative coupling between controller component 310 and probe component 312.

In an aspect, controller component 310 can receive an analysis and can then institute the analysis via a portable analytical equipment device comprising controller component 310. To this end, controller component 310 can comprise analytics portfolio component 330. Analytics portfolio component 330 can enable storage of one or more analysis, e.g., in an analysis portfolio, etc. In some embodiments, controller component 310 can comprise a memory or storage device that, via analytics portfolio component 330, can have stored thereon one or more analysis. In an aspect, the memory or storage device can comprise a portfolio of analyses comprising the one or more analysis. An analysis can be defined and stored in the portfolio via analytics portfolio component 330 to allow the analysis to be selected via analytics portfolio component 330 from the portfolio. The stored analysis can comprise parameters and settings.

Analytics portfolio component 330 can enable different analyses to be readily selected and employed. Analytics portfolio component 330 can select an analysis, e.g., from a portfolio of analyses, based on determined parameters and inputs, e.g., inputs from a local or remote user. The parameters can be related to operational conditions, environments, schedules, historical results, historical operations, etc. As an example, analytics portfolio component 330 can select an analysis that averages more results based on a prior analysis generating results that had levels of noise exceeding a determined threshold. As another example, analytics portfolio component 330 can select an analysis that is suited to a particular sample environment based on a determined location in a facility, e.g., a sugar analysis when analytics portfolio component 330 determines that the device is near a wort liquid line and an alcohol analysis when analytics portfolio component 330 determines that the device is near a distillation line. Parametric selection and/or rules-based selection of an analysis by analytics portfolio component 330 can enable device operation without an operator needing to manually select an analysis because analytics portfolio component 330 can determine which analysis should be selected based on the parameter values and/or rules related to selection of an analysis. Moreover, analytics portfolio component 330 can select an analysis with, or without, wired or wireless connectivity. In embodiments where the portfolio is stored on an external storage device, e.g., a flash drive that can be plugged into, e.g., connected to controller component 310 via analytics portfolio component 330, an analysis can be selected therefrom. Further, the removable storage device can allow rapid selection of another portfolio of analyses by simply swapping the removable storage device for another having stored thereon a different portfolio of analyses. In additional embodiments, the portfolio of analyses can be stored on another device, e.g., a smartphone, laptop, tablet computer, etc., or a remotely located device, server, remotely located computer, etc., allowing, via analytics portfolio component 330, execution of an analysis from nearly any source. Where the portfolio is located other than at controller component 310, a communicative coupling between the portfolio and analytics portfolio component 330 can be employed to allow the analysis to be 'loaded' into controller component 310 for execution. In contrast, a portfolio in a memory of storage device of controller component 310 can operate without such a communicative coupling to external resources, e.g., no connection to a remote server is needed to perform the analysis when the analysis is selected by analytics portfolio component 330 from a portfolio stored on a memory of controller component 310.

In another aspect, controller component 310 can comprise spectral library component 320 to enable performing an analysis in accord with a received analysis, e.g., from a portfolio of analyses, based on reference spectral analysis data. Reference spectral analysis data can be received by controller component 310. In an aspect, reference spectral analysis data can be stored on a memory or storage device of controller component 310, e.g., spectral library component 320. As an example, Raman spectra for known chemical compounds, e.g., a Raman spectral library, can be stored by spectral library component 320 on a memory of a portable analytical equipment device comprising controller component 310. The results of a Raman interrogation of a sample can be compared to the Raman spectral library to facilitate analysis of the results of the Raman interrogation. In an aspect, stored reference spectral analytical data can be tailored to particular applications. In some embodiments, reference spectral analysis data can be received by controller component 310 from other local or remotely located memory, e.g., a local UE such as UE 440, from a remote server, from a cloud-based spectral library component, etc.

In an embodiment, controller component 310 can initiate an analysis, selected via analytics portfolio component 330, in response to a received trigger. In an aspect, the trigger can be caused by an operator, e.g., a user presses a button, shakes the device, etc. In another aspect, the trigger can be associated with a received analysis. The received analysis can designate a trigger value, such a timed intervals, time of day, scheduled times, analysis on a detected change in a sampling environment, etc. In a further aspect, controller component 310 can receive an analysis that limits initiation of an analysis to certain conditions, e.g., when temperature is between two set points, when a battery is above a threshold charge level, etc.

In an embodiment, controller component can enable operation of portable analytical equipment that does not comprise an embedded LCD-type display, e.g., comparable to a modern smartphone display, for example image 301 illustrates an example device that lacks an integrated LCD-type display. By dispensing with an integrated display, controller component 310 can be employed in a smaller form factor than conventional portable analytical equipment. Further, where an integrated display is not employed, operational life between charging/swapping a battery can be improved over conventional portable analytical equipment. Moreover, in some embodiments, controller component 310 can support operation of an indicator that can be employed to communicate comparatively basic information to a user/operator, e.g., a green light can indicate a pass/safe/undetected while a red light can indicate a fail/danger/detected. While an indicator can comprise much less detailed information than can typically be presented via an LCD-type display, the inherently simple nature of the indicator can be advantageous over integrated displays.

In an aspect, controller component 310 can employ an indicator to allow a user/operator to operate the device meaningfully with little training. In contrast to an integrated LCD display, which can need skilled interpretation, an indicator can communicate basic, but still meaningful information, to an operator, even those with low skill levels. As such, detection can be communicated without needing to train the operator to interpret a displayed result, such as a displayed optical spectrum. The user can therefore be aware of detection result and can then determine any need for further testing, a need to have results reviewed by a more highly trained operator, etc.

In a further aspect, use of indicators by controller component 310 can consume less power than typically associated with a conventional LCD-type display, allowing for fielded portable analytical equipment to either be smaller and/or operate for longer periods of time. In some embodiments, other "low-power" indicators, meaning any indicator consuming less power than a typical embedded LCD-type display, can include one or more multicolored LEDs, one or more single color LEDs, LEDs arranged in patterns, etc. However, LEDs can still drain a battery over extended periods of time, though not nearly as quickly as an LCD-type display. Where even lower power consumption can be desirable, some embodiments can comprise controller component 310 control of flag-type devices, e.g., mechanical flags, electrophoretics, etc.

In yet another aspect, where there is no display incorporated into the portable analytical equipment, the device can be more rugged, e.g., there is no screen to crack or break, meaning that the portable analytical equipment can be deployed without bulky and weighty protective cases than might be associated with conventional portable analytical equipment. Still further, in some embodiments of the presently disclosed subject matter, the portable analytical equipment comprising controller component 310 and probe component 312 can be made small enough to simply slip into a pocket, pouch on a backpack, glovebox, etc., as illustrated by the example device shown in image 301. Separating a conventional LCD-type display from portable analytical equipment can also lower manufacturing, wholesale, and retail monetary costs.

In an embodiment, controller component 310 can be communicatively coupled with another device (not illustrated), e.g., a laptop, smartphone, tablet, etc., to allow interaction with controller component 310 via the other device. The other coupled device can provide a display for visualizing and/or interacting with analytical results that would be generally comparable to, or better than, conventional portable analytical equipment with an embedded display, e.g., coupling to a smartphone can provide similar display area and resolution as conventional portable analytical equipment, and coupling to a tablet or laptop can provide a display that is frequently larger and/or better resolution that displays comprised in conventional portable analytical equipment. Additionally, the increasing performance of these other devices can allow the presently disclosed portable analytical equipment to remain highly relevant where external devices continue to evolve. This can be a considerable advantage over conventional portable analytical equipment because these improving technologies can then be leveraged to provide an improved user experience as they come to market.

In a further aspect, controller component 310 can comprise wired and wireless connectivity. This can enable connection with a local external device, e.g., a laptop, smartphone, tablet, etc., as well as remotely located devices, for visualizing and interacting with the controller component 310. In an embodiment, controller component 310 can connect to remotely located devices via a wired or wireless interface, e.g., cellular, Wi-Fi, Bluetooth, etc. This can facilitate communication of information via a communications infrastructure, intranet, internet, WAN, LAN, ad-hoc networks, etc. In some embodiments, results of analytical interrogations can be communicated to these remote devices by controller component 310. This can include real-time, or near-real time, communication of interrogation results, as well as bundling sets of results and transmitting them together, e.g., burst transmission of analytical interrogation results. Moreover, in some embodiments, information can be communicated to controller component 310, e.g., control data, updating an a portfolio of analyses or analysis thereof, running diagnostics, checking a status, triggering execution of an analysis, requesting data transmission, etc., can be sent to controller component 310 via a wired or wireless interface of controller component 310.

In some embodiments, controller component 310 can comprise a remote deployment interface component. This can facilitate remote deployment of a device comprising controller component 310. The remote deployment interface can comprise a wired/wireless communications interface, an external power interface, e.g., solar power, external battery, power over Ethernet (POE), mains power connectivity, etc., external memory and/or storage device interface, etc. The remote deployment interface can enable portable analytical equipment comprising controller component 310 to be readily remotely deployed.

In some embodiments, controller component 310 and probe component 312 can be packaged in a hand held device. This small form factor can be facilitated by employing indicators in lieu of incorporating a conventional LCD-type display in to the hand held device. This small form factor can further be facilitated by employing a retractable probe component 312, such as a retractable BallProbe™. This small form factor can also be facilitated by employing a smaller battery than might be needed in a conventional device due to power consumption by a conventional LCD-type display. Of note, small, low cost, rugged, and capable portable analytical equipment can be highly desired in many fields using analytical equipment, more especially where training of operators can be substantially reduced. The presently disclosed subject matter, such as system 300, can facilitate these types of portable analytical equipment.

Figure 4:
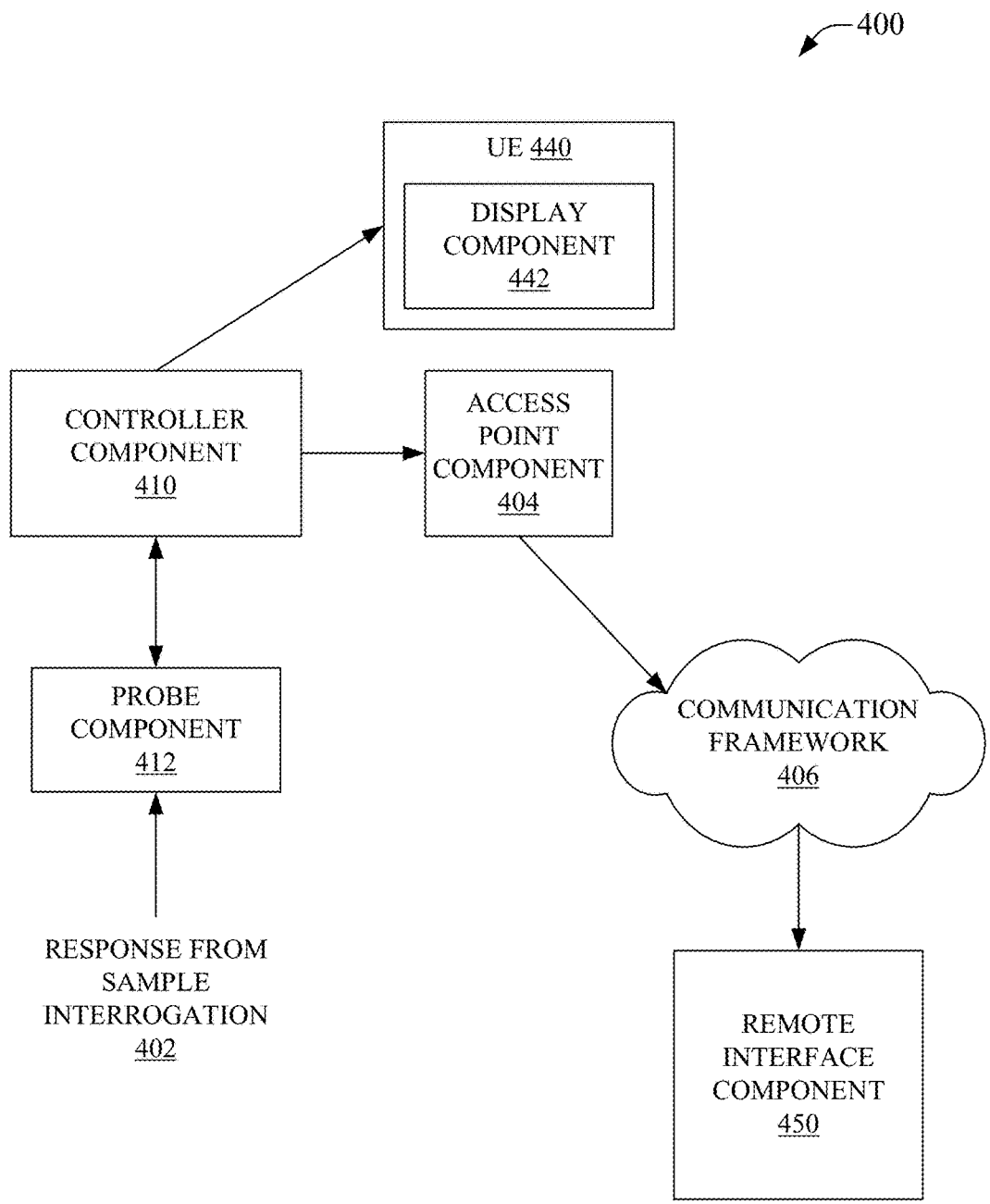
FIG. 4 illustrates an example system that facilitates portable analytical equipment coupled to external components to facilitate additional analytical features and/or control features in accordance with aspects of the subject disclosure.

FIG. 4 illustrates a system 400 that facilitates portable analytical equipment coupled to external components to facilitate additional analytical features and/or control features in accordance with aspects of the subject disclosure. System 400 can comprise controller component 410. Controller component 410 can control execution of an analytical interrogation, e.g., via probe component 412. Controller component 410 can further control execution of an analysis related to the analytical interrogation, e.g., in response to receiving response from sample interrogation 402 via probe component 412. Additionally, controller component 410 can control interactions with a user/operator, e.g., via a user interface, via other devices, etc. In an aspect, controller component 410 can enable presentation of an indicator related to a result of analysis, e.g., via a low-power user interface, via other devices, e.g., 440, etc., coupled to controller component 410, via other devices, e.g., 450, etc., located remotely and coupled to controller component 410 via network components, e.g., 404, etc., such as a Wi-Fi access point, etc.

Controller component 410 can be communicatively coupled to probe component 412. In some embodiments, probe component can be part of, or integrated with, controller component 410, e.g., the probe can be mechanically attached to a housing that houses controller component 410 to form a portable analytical equipment device, see for example the example portable analytical equipment device depicted in image 301. In an aspect, probe component 412 can be retractable, in whole or in part, allowing devices comprising probe component 412 and controller component 410 to be more compact in a probe-retracted configuration than in a probe-extended configuration. In other embodiments, probe component 412 can be flexibly connected to controller component 410. In an aspect, probe component 412 can comprise a 'goose-neck' type flexible portion, a pivot portion, a rotatable portion, etc., allowing the disposition of probe component 412 relative to controller component 410 to be adapted in the field. In further embodiments, probe component 412 can be coupled to controller component 410 via a conductor and/or a fiber optic. This can allow probe component 412 to be deployable in a manner that is nearly unrelated to the deployment of controller component 410. In an embodiment, probe component 412 can comprise a BallProbe™ (MarqMetrix Inc., Seattle, Wash.). Ball Probe™ can enable Raman spectrometry of an environment. In an aspect, the BallProbe™ can allow for in-situ Raman spectrometry via probe component 412. The BallProbe™ can be controlled by controller component 410 via the communicative coupling between controller component 410 and probe component 412.

In an aspect, controller component 410 can receive an analysis and can then institute the analysis via a portable analytical equipment device comprising controller component 410. To this end, controller component 410 can comprise an analytics portfolio component, not illustrated. Analytics portfolio component can enable storage of one or more analysis, e.g., in an analysis portfolio, etc. In some embodiments, controller component 410 can comprise a memory or storage device that, via analytics portfolio component, can have stored thereon one or more analysis. In an aspect, the memory or storage device can comprise a portfolio of analyses comprising the one or more analysis. An analysis can be defined and stored in the portfolio via analytics portfolio component to allow the analysis to be selected via analytics portfolio component from the portfolio. The stored analysis can comprise parameters and settings related to one or more analysis. An analytics portfolio component can enable different analyses to be readily selected and employed. An analytics portfolio component can select an analysis, e.g., from a portfolio of analyses, based on determined parameters and inputs, e.g., inputs from a local or remote user, such as via UE 440, or via remote interface component 450, etc. The parameters can be related to operational conditions, environments, schedules, historical results, historical operations, etc. Parametric selection and/or rules-based selection of an analysis by an analytics portfolio component can enable device operation without an operator needing to manually select an analysis because the analytics portfolio component can determine which analysis should be selected based on the parameter values and/or rules related to selection of an analysis. Moreover, an analytics portfolio component can select an analysis with, or without, wired or wireless connectivity. In embodiments where the portfolio is stored on an external storage device, e.g., a flash drive that can be plugged into, e.g., connected to controller component 410 via an analytics portfolio component, an analysis can be selected therefrom. Further, the removable storage device can allow rapid selection of another portfolio of analyses by simply swapping the removable storage device for another having stored thereon a different portfolio of analyses. In additional embodiments, the portfolio of analyses can be stored on another device, e.g., UE 440, etc., or a remotely located device, e.g., 450, etc., allowing, via an analytics portfolio component, execution of an analysis from nearly any source. Where the portfolio is located other than at controller component 410, a communicative coupling between the portfolio and the analytics portfolio component can be employed to allow the analysis to be 'loaded' into controller component 410 for execution.

In another aspect, controller component 410 can comprise a spectral library component, not illustrated, to enable performing an analysis in accord with a received analysis, e.g., from a portfolio of analyses, based on reference spectral analysis data. Reference spectral analysis data can be received by controller component 410. In an aspect, reference spectral analysis data can be stored on a memory or storage device of controller component 410, e.g., a spectral library component. As an example, Raman spectra for known chemical compounds, e.g., a Raman spectral library, can be stored by a spectral library component on a memory of a portable analytical equipment device comprising controller component 410. The results of a Raman interrogation of a sample can be compared to the Raman spectral library to facilitate analysis of the results of the Raman interrogation. In an aspect, stored reference spectral analytical data can be tailored to particular applications. In some embodiments, the spectral library can be stored on removable memory that can be connected with controller component 410, e.g., wired or wirelessly, stored on a memory or a local or remote device or system, e.g., on a memory of UE 440, on a memory related to remote interface component 450, etc., e.g., a cloud-based spectral library, etc.

In an embodiment, controller component 410 can initiate an analysis, e.g., selected via an analytics portfolio component, in response to a received trigger. In an aspect, the trigger can be caused by an operator, e.g., a user presses a button, shakes the device, etc. In another aspect, the trigger can be associated with a received analysis. The received analysis can designate a trigger value, such a timed intervals, time of day, scheduled times, analysis on a detected change in a sampling environment, etc. In a further aspect, controller component 410 can receive an analysis that limits initiation of an analysis to certain conditions, e.g., when temperature is between two set points, when a battery is above a threshold charge level, etc. In some embodiments, controller component can receive a trigger from an external device, e.g., 440, 450, etc.

In an embodiment, controller component can enable operation of portable analytical equipment that does not comprise an embedded LCD-type display, e.g., comparable to a modern smartphone display. By dispensing with an integrated display, controller component 410 can be employed in a smaller form factor than conventional portable analytical equipment. Further, where an integrated display is not employed, operational life between charging/swapping a battery can be improved over conventional portable analytical equipment. Moreover, in some embodiments, controller component 410 can support operation of an indicator that can be employed to communicate comparatively basic information to a user/operator, e.g., a green light can indicate a pass/safe/undetected while a red light can indicate a fail/danger/detected. While an indicator can comprise much less detailed information than can typically be presented via an LCD-type display, the inherently simple nature of the indicator can be advantageous over integrated displays.

In an aspect, controller component 410 can employ an indicator to allow a user/operator to operate the device meaningfully with little training. In contrast to an integrated LCD display, which can need skilled interpretation, an indicator can communicate basic, but still meaningful information, to an operator, even those with low skill levels. As such, detection can be communicated without needing to train the operator to interpret a displayed result, such as a displayed optical spectrum. The user can therefore be aware of detection result and can then determine any need for further testing, a need to have results reviewed by a more highly trained operator, etc.

In a further aspect, use of indicators by controller component 410 can consume less power than typically associated with a conventional LCD-type display, allowing for fielded portable analytical equipment to either be smaller and/or operate for longer periods of time. In some embodiments, other "low-power" indicators, meaning any indicator consuming less power than a typical embedded LCD-type display, can include one or more multicolored LEDs, one or more single color LEDs, LEDs arranged in patterns, etc. However, LEDs can still drain a battery over extended periods of time, though not nearly as quickly as an LCD-type display. Where even lower power consumption can be desirable, some embodiments can comprise controller component 410 control of flag-type devices, e.g., mechanical flags, electrophoretics, etc.

In yet another aspect, where there is no display incorporated into the portable analytical equipment, the device can be more rugged, e.g., there is no screen to crack or break, meaning that the portable analytical equipment can be deployed without bulky and weighty protective cases than might be associated with conventional portable analytical equipment. Still further, in some embodiments of the presently disclosed subject matter, the portable analytical equipment comprising controller component 410 and probe component 412 can be made small enough to simply slip into a pocket, pouch on a backpack, glovebox, etc. Separating a conventional LCD-type display from portable analytical equipment can also lower manufacturing, wholesale, and retail monetary costs.

In an embodiment, controller component 410 can be communicatively coupled with UE 440, e.g., a laptop, smartphone, tablet, etc., to allow interaction with controller component 410 via UE 440. The UE 440 can provide a display, e.g., display component 442, for visualizing and/or interacting with analytical results that would be generally comparable to, or better than, conventional portable analytical equipment with an embedded display, e.g., coupling to a smartphone can provide similar display area and resolution as conventional portable analytical equipment, and coupling to a tablet or laptop can provide a display that is frequently larger and/or better resolution that displays comprised in conventional portable analytical equipment. Additionally, the increasing performance of these other devices can allow the presently disclosed portable analytical equipment to remain highly relevant where external devices, e.g., UE 440, continue to evolve. This can be a considerable advantage over conventional portable analytical equipment because these improving technologies can then be leveraged to provide an improved user experience as they come to market.

In a further aspect, controller component 410 can comprise wired and wireless connectivity. This can enable connection with a local external device, e.g., UE 440, as well as remotely located devices via remote interface component 450, for visualizing and interacting with the controller component 410. In an embodiment, controller component 410 can connect to remote interface component 450 via a wired or wireless interface, e.g., access point component 404, etc. This can facilitate communication of information via communications framework 406, e.g., intranet, internet, WAN, LAN, ad-hoc networks, etc. In some embodiments, results of analytical interrogations can be communicated to remote interface component 450 by controller component 410. This can include real-time, or near-real time, communication of interrogation results, as well as bundling sets of results and transmitting them together, e.g., burst transmission of analytical interrogation results. As such, for example, interrogation results can be communicated to a remote system, not illustrated, where a some, or all, of an analysis can be performed, e.g., cloud-based analysis, and results can be returned back to controller component 410, thereby offloading many computationally intense aspects of controller component 410 to remoted devices. Moreover, in some embodiments, information can be communicated to controller component 410 from remote interface component 450, e.g., control data, updating an a portfolio of analyses or analysis thereof, running diagnostics, checking a status, triggering execution of an analysis, requesting data transmission, etc., can be sent to controller component 410 from remote interface component 450 via communication framework 406, etc.

In some embodiments, controller component 410 can comprise a remote deployment interface component, not illustrated. This can facilitate remote deployment of a device comprising controller component 410. The remote deployment interface can comprise a wired/wireless communications interface, an external power interface, e.g., solar power, external battery, power over Ethernet (POE), mains power connectivity, etc., external memory and/or storage device interface, etc. The remote deployment interface can enable portable analytical equipment comprising controller component 410 to be readily remotely deployed.

In some embodiments, controller component 410 and probe component 412 can be packaged in a hand held device. This small form factor can be facilitated by employing indicators in lieu of incorporating a conventional LCD-type display in to the hand held device. This small form factor can further be facilitated by employing a retractable probe component 412, such as a retractable BallProbe™. This small form factor can also be facilitated by employing a smaller battery than might be needed in a conventional device due to power consumption by a conventional LCD-type display. Of note, small, low cost, rugged, and capable portable analytical equipment can be highly desired in many fields using analytical equipment, more especially where training of operators can be substantially reduced. The presently disclosed subject matter, such as system 400, can facilitate these types of portable analytical equipment.

Figure 5:
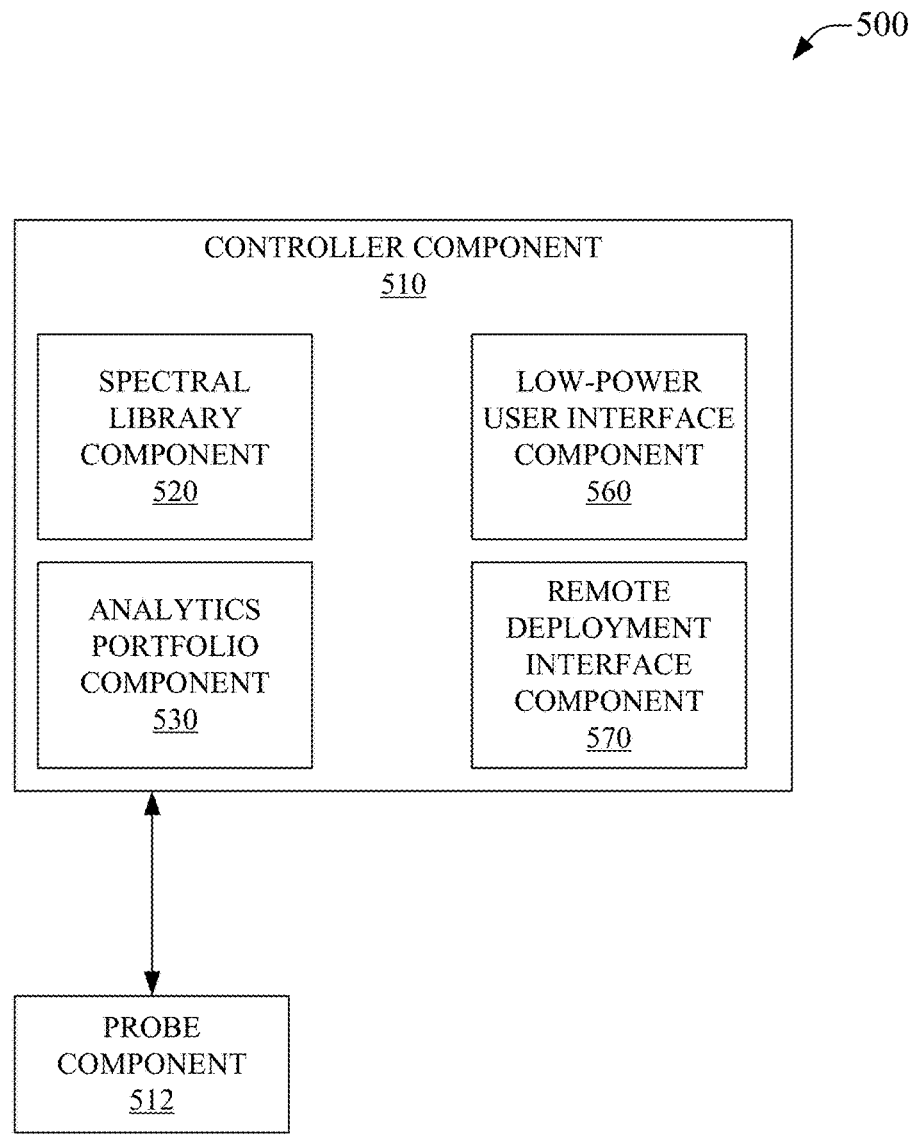
FIG. 5 illustrates an example system that facilitates portable spectral analysis equipment comprising a low-power user interface and a remote deployment interface in accordance with aspects of the subject disclosure.

FIG. 5 illustrates a system 500 that facilitates portable spectral analysis equipment comprising a low-power user interface and a remote deployment interface in accordance with aspects of the subject disclosure. System 500 can comprise controller component 510. Controller component 510 can control execution of an analytical interrogation, e.g., via probe component 512. Controller component 510 can further control execution of an analysis related to the analytical interrogation, e.g., in response to receiving response from sample interrogation via probe component 512. Additionally, controller component 510 can control interactions with a user/operator, e.g., via a user interface, via other devices, etc. In an aspect, controller component 510 can enable presentation of an indicator related to a result of analysis, e.g., via a low-power user interface, via other devices coupled to controller component 510, via other devices located remotely and coupled to controller component 510 via network components such as a Wi-Fi access point, etc.

Controller component 510 can be communicatively coupled to probe component 512. In some embodiments, probe component can be part of, or integrated with, controller component 510. In an aspect, probe component 512 can be retractable, in whole or in part, allowing devices comprising probe component 512 and controller component 510 to be more compact in a probe-retracted configuration than in a probe-extended configuration. In other embodiments, probe component 512 can be flexibly connected to controller component 510. In further embodiments, probe component 512 can be coupled to controller component 510 via a conductor and/or a fiber optic. This can allow probe component 512 to be deployable in a manner that is nearly unrelated to the deployment of controller component 510. In an embodiment, probe component 512 can comprise a BallProbe™ (MarqMetrix Inc., Seattle, Wash.). Ball Probe™ can enable Raman spectrometry of an environment. In an aspect, the BallProbe™ can allow for in-situ Raman spectrometry via probe component 512. The BallProbe™ can be controlled by controller component 510 via the communicative coupling between controller component 510 and probe component 512.

In an aspect, controller component 510 can receive an analysis and can then institute the analysis via a portable analytical equipment device comprising controller component 510. In some embodiments, controller component 510 can comprise a memory or storage device that can have stored thereon one or more analysis. In an aspect, the memory or storage device can comprise a portfolio of analyses comprising the one or more analysis. An analysis can be defined and stored in the portfolio to allow the analysis to be selected from the portfolio. An analysis can be selected, e.g., from a portfolio of analyses, based on determined parameters and inputs. The parameters can be related to operational conditions, environments, schedules, historical results, historical operations, etc. Parametric selection and/or rules-based selection of an analysis can enable device operation without an operator needing to manually select an analysis because selection of an analysis can be based on the parameter values and/or rules related to selection of an analysis.

In another aspect, controller component 510 can performing an analysis in accord with a received analysis, e.g., from a portfolio of analyses, based on reference spectral analysis data. Reference spectral analysis data can be received by controller component 510. In an aspect, reference spectral analysis data can be stored on a memory or storage device of controller component 510. As an example, Raman spectra for known chemical compounds, e.g., a Raman spectral library, can be stored on a memory of a portable analytical equipment device comprising controller component 510. The results of a Raman interrogation of a sample can be compared to the Raman spectral library to facilitate analysis of the results of the Raman interrogation. In an aspect, stored reference spectral analytical data can be tailored to particular applications.

In an embodiment, controller component 510 can initiate an analysis in response to a received trigger. In an aspect, the trigger can be caused by an operator, e.g., a user presses a button, shakes the device, etc. In another aspect, the trigger can be associated with a received analysis. The received analysis can designate a trigger value, such as timed intervals, time of day, scheduled times, analysis on a detected change in a sampling environment, etc. In a further aspect, controller component 510 can receive an analysis that limits initiation of an analysis to certain conditions, e.g., when temperature is between two set points, when a battery is above a threshold charge level, etc.

In an embodiment, controller component 510 can comprise low-power user interface component 560. Low-power user interface component 560 can enable operation of portable analytical equipment that does not comprise an embedded LCD-type display, e.g., comparable to a modern smartphone display. By dispensing with an integrated display, controller component 510 can be employed in a smaller form factor than conventional portable analytical equipment. Further, where an integrated display is not employed, operational life between charging/swapping a battery can be improved over conventional portable analytical equipment. Low-power user interface component 560 can support operation of an indicator that can be employed to communicate comparatively basic information to a user/operator, e.g., a green LED can indicate a pass/safe/undetected while a red LED can indicate a fail/danger/detected. While an indicator can comprise much less detailed information than can typically be presented via an LCD-type display, the inherently simple nature of the indicator can be advantageous over integrated displays.

In an aspect, low-power user interface component 560 can comprise an indicator to allow a user/operator to operate the device meaningfully with little training. In contrast to an integrated LCD display, which can need skilled interpretation, an indicator can communicate basic, but still meaningful information, to an operator, even those with low skill levels. As such, detection can be communicated without needing to train the operator to interpret a complex LCD displayed result, such as a displayed optical spectrum. The user can therefore be aware of detection result and can then determine any need for further testing, a need to have results reviewed by a more highly trained operator, etc.

In a further aspect, use of indicators by low-power user interface component 560 can consume less power than typically associated with a conventional LCD-type display, allowing for fielded portable analytical equipment to either be smaller and/or operate for longer periods of time. In some embodiments, low-power user interface component 560 can comprise other "low-power" indicators, meaning any indicator consuming less power than a typical embedded LCD-type display, which can include one or more multicolored LEDs, one or more single color LEDs, LEDs arranged in patterns, etc. However, LEDs can still drain a battery over extended periods of time, though not nearly as quickly as an LCD-type display. Where even lower power consumption can be desirable, some embodiments of low-power user interface component 560 can comprise flag-type devices, electrophoretics, etc.

In yet another aspect, where there is no display incorporated into the portable analytical equipment due to employing low-power user interface component 560, the device can be more rugged, e.g., there is no screen to crack or break, meaning that the portable analytical equipment can be deployed without bulky and weighty protective cases than might be associated with conventional portable analytical equipment. Still further, in some embodiments of the presently disclosed subject matter, controller component 510 comprising low-power user interface component 560 and probe component 512 can be made small enough to simply slip into a pocket, pouch on a backpack, glovebox, etc. Separating a conventional LCD-type display and incorporating low-power user interface component 560 into portable analytical equipment can also lower manufacturing, wholesale, and retail monetary costs.

In an embodiment, controller component 510 can be communicatively coupled with another device (not illustrated), e.g., a laptop, smartphone, tablet, etc., to allow interaction with controller component 510 via the other device. The other coupled device can provide a display for visualizing and/or interacting with analytical results that would be generally comparable to, or better than, conventional portable analytical equipment with an embedded display, e.g., coupling to a smartphone can provide similar display area and resolution as conventional portable analytical equipment, and coupling to a tablet or laptop can provide a display that is frequently larger and/or better resolution that displays comprised in conventional portable analytical equipment. Additionally, the increasing performance of these other devices can allow the presently disclosed portable analytical equipment to remain highly relevant where external devices continue to evolve. This can be a considerable advantage over conventional portable analytical equipment because these improving technologies can then be leveraged to provide an improved user experience as they come to market.

In a further aspect, controller component 510 can comprise wired and wireless connectivity. This can enable connection with a local external device, e.g., a laptop, smartphone, tablet, etc., as well as remotely located devices, for visualizing and interacting with the controller component 510. In an embodiment, controller component 510 can connect to remotely located devices via a wired or wireless interface, e.g., cellular, Wi-Fi, Bluetooth, etc. This can facilitate communication of information via a communications infrastructure, intranet, internet, WAN, LAN, ad-hoc networks, etc. In some embodiments, results of analytical interrogations can be communicated to these remote devices by controller component 510. This can include real-time, or near-real time, communication of interrogation results, as well as bundling sets of results and transmitting them together, e.g., burst transmission of analytical interrogation results. Moreover, in some embodiments, information can be communicated to controller component 510, e.g., control data, updating an a portfolio of analyses or analysis thereof, running diagnostics, checking a status, triggering execution of an analysis, requesting data transmission, etc., can be sent to controller component 510 via a wired or wireless interface of controller component 510.

In some embodiments, controller component 510 can comprise remote deployment interface component 570. Remote deployment interface component 570 can facilitate remote deployment of a device comprising controller component 510. Remote deployment interface component 570 can comprise a wired/wireless communications interface, an external power interface, e.g., solar power, external battery, power over Ethernet (POE), mains power connectivity, etc., external memory and/or storage device interface, etc. Remote deployment interface component 570 can enable portable analytical equipment comprising controller component 510 to be readily remotely deployed.

In some embodiments, controller component 510 and probe component 512 can be packaged in a hand held device. This small form factor can be facilitated by employing indicators in lieu of incorporating a conventional LCD-type display in to the hand held device. This small form factor can further be facilitated by employing a retractable probe component 512, such as a retractable BallProbe™. This small form factor can also be facilitated by employing a smaller battery than might be needed in a conventional device due to power consumption by a conventional LCD-type display. Of note, small, low cost, rugged, and capable portable analytical equipment can be highly desired in many fields using analytical equipment, more especially where training of operators can be substantially reduced. The presently disclosed subject matter, such as system 500, can facilitate these types of portable analytical equipment.

Figure 6:
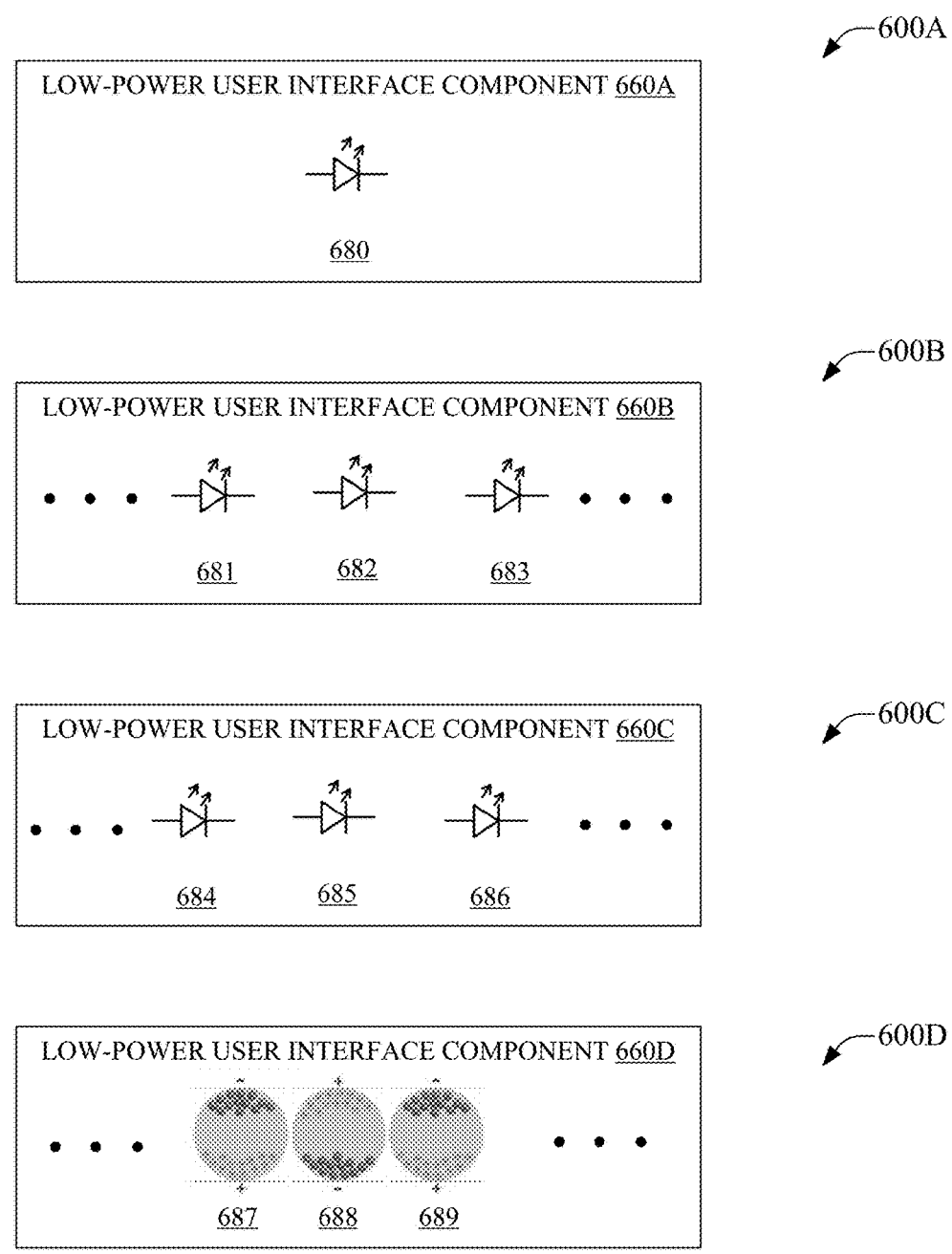
FIG. 6 illustrates example systems depicting low-power user interface components comprising low-power indicator techniques in accordance with aspects of the subject disclosure.

FIG. 6 illustrates systems 600A-D depicting low-power user interface components comprising low-power indicator techniques in accordance with aspects of the subject disclosure. System 600A can comprise low-power user interface component 660A, system 600B can comprise low-power user interface component 660B, system 600C can comprise low-power user interface component 660C, and system 600D can comprise low-power user interface component 660D, that can each enable operation of portable analytical equipment that does not comprise an embedded LCD-type display, e.g., comparable to a modern smartphone display. By dispensing with an integrated display, a controller component can be employed in a smaller form factor than conventional portable analytical equipment. Further, where an integrated display is not employed, operational life between charging/swapping a battery can be improved over conventional portable analytical equipment. Low-power user interface components 660A-D can support operation of an indicator that can be employed to communicate comparatively basic information to a user/operator. While an indicator can comprise much less detailed information than can typically be presented via an LCD-type display, the inherently simple nature of the indicator can be advantageous over integrated displays.

In an aspect, low-power user interface components 660A-D can comprise an indicator to allow a user/operator to operate the device meaningfully with little training. In contrast to an integrated LCD display, which can need skilled interpretation, an indicator can communicate basic, but still meaningful information, to an operator, even those with low skill levels. As such, detection can be communicated without needing to train the operator to interpret a complex LCD displayed result, such as a displayed optical spectrum. The user can therefore be aware of detection result and can then determine any need for further testing, a need to have results reviewed by a more highly trained operator, etc.

In a further aspect, use of indicators by low-power user interface components 660A-D can consume less power than typically associated with a conventional LCD-type display, allowing for fielded portable analytical equipment to either be smaller and/or operate for longer periods of time. In some embodiments, low-power user interface components 660A-D can comprise "low-power" indicators, meaning any indicator consuming less power than a typical embedded LCD-type display, which can include one or more multicolored LEDs, one or more single color LEDs, LEDs arranged in patterns, etc. However, LEDs can still drain a battery over extended periods of time, though not nearly as quickly as an LCD-type display. Where even lower power consumption can be desirable, some embodiments of low-power user interface components 660A-D can comprise flag-type devices, electrophoretics, etc.

In yet another aspect, where there is no display incorporated into the portable analytical equipment due to employing low-power user interface components 660A-D, the device can be more rugged, e.g., there is no screen to crack or break, meaning that the portable analytical equipment can be deployed without bulky and weighty protective cases than might be associated with conventional portable analytical equipment. Still further, in some embodiments of the presently disclosed subject matter, a controller component comprising low-power user interface components 660A-D and a probe component can be made small enough to simply slip into a pocket, pouch on a backpack, glovebox, etc. Separating a conventional LCD-type display and incorporating low-power user interface components 660A-D into portable analytical equipment can also lower manufacturing, wholesale, and retail monetary costs.

In an embodiment, a controller component can be communicatively coupled with another device (not illustrated), e.g., a laptop, smartphone, tablet, etc., to allow interaction with the controller component via the other device. The other coupled device can provide a display for visualizing and/or interacting with analytical results that would be generally comparable to, or better than, conventional portable analytical equipment with an embedded display, e.g., coupling to a smartphone can provide similar display area and resolution as conventional portable analytical equipment, and coupling to a tablet or laptop can provide a display that is frequently larger and/or better resolution that displays comprised in conventional portable analytical equipment. Additionally, the increasing performance of these other devices can allow the presently disclosed portable analytical equipment to remain highly relevant where external devices continue to evolve. This can be a considerable advantage over conventional portable analytical equipment because these improving technologies can then be leveraged to provide an improved user experience as they come to market.

Low-power user interface component 660A can comprise LED 680. LED 680 can be a one color LED or a multicolor LED. Similarly, low-power user interface component 660B can comprise LEDs 681-683. LEDs 681-683 can each be the same as or similar to LED 680. In 600B, low-power user interface component 660B can arrange a plurality of LEDs, e.g., LEDs 681-683, in an array, matrix or other pattern, such that the order of illumination of LEDs 681-683 can communicate information to an observer. As an example, where LED 681 is green, LED 682 is yellow, and LED 683 is red, illumination LED 681 can indicate a first condition, illumination LED 682 can indicate a second condition, and illumination LED 683 can indicate a third condition. These conditions can represent low/medium/high levels of a compound being detected, safe/caution/danger, etc. Further, as an example, flashing LEDs 681-683 can indicate a fault condition, failed analysis, low battery condition, or other information.

Low-power user interface component 660C can also comprise LEDs, e.g., 684-686. LEDs 684-686 can each be the same as or similar to LED 680. In 600C, low-power user interface component 660C can arrange a plurality of LEDs, e.g., LEDs 684-686, in an array, matrix or other pattern, such that the pattern of illuminated/unilluminated LEDs 684-686 can communicate information to an observer. As an example, where an 'x' represents unilluminated and an 'o' represents illuminated, LEDs 684-686 showing 'xox' can indicate a first condition, 'oxo' can indicate a second condition, 'xxx' can indicate a third condition, etc., such that were there are n LEDs, $2^n$ conditions can be represented. These conditions can represent low/medium/high levels of a compound being detected, safe/caution/danger, etc. Further, apparent motion of LEDs, e.g., sequential illumination of LEDs, can provide additional information, where a left-moving pattern of illumination indicates condition $2^n+1$, right-moving pattern of illumination indicates condition $2^n+2$, upward-moving pattern of illumination indicates condition $2^n+3$, etc. Further, as an example, flashing LEDs 684-686 can indicate a fault condition, failed analysis, low battery condition, or nearly any other condition or information.

Low-power user interface component 660D of system 600D can comprise electrophoretics elements 687-689 in place of LED elements. Low-power user interface component 660D can comprise one or more electrolphoretic element(s), though a plurality are illustrated. Electrophoretic element(s) 687-689 can be arranged in a manner similar to, or the same as, LEDs 680-686 and can indicate similar conditions. Moreover, electrophoretic elements can enable depictions of color, symbols, letters, words, numbers, etc. As an example, a sufficiently large array of electrophoretic elements can communicate words, sentences, etc., such as 'DANGER', 'FAULT', 'TESTING', 'ACQUIRING', 'CO2 DETECTED', etc. In some embodiments, display sized panels of electrophoretic elements can substitute for an LCD-type display while retaining many low-power advantages, however, these large displays reduce the ability to keep devices compact, light, and rugged. Where the design tradeoffs are acceptable, electrophoretic elements can be employed in any number, although small hand-held devices are envisioned with lower numbers of elements sufficient to communicate information in a manner similar to, or the same as, LEDs.

Figure 7:
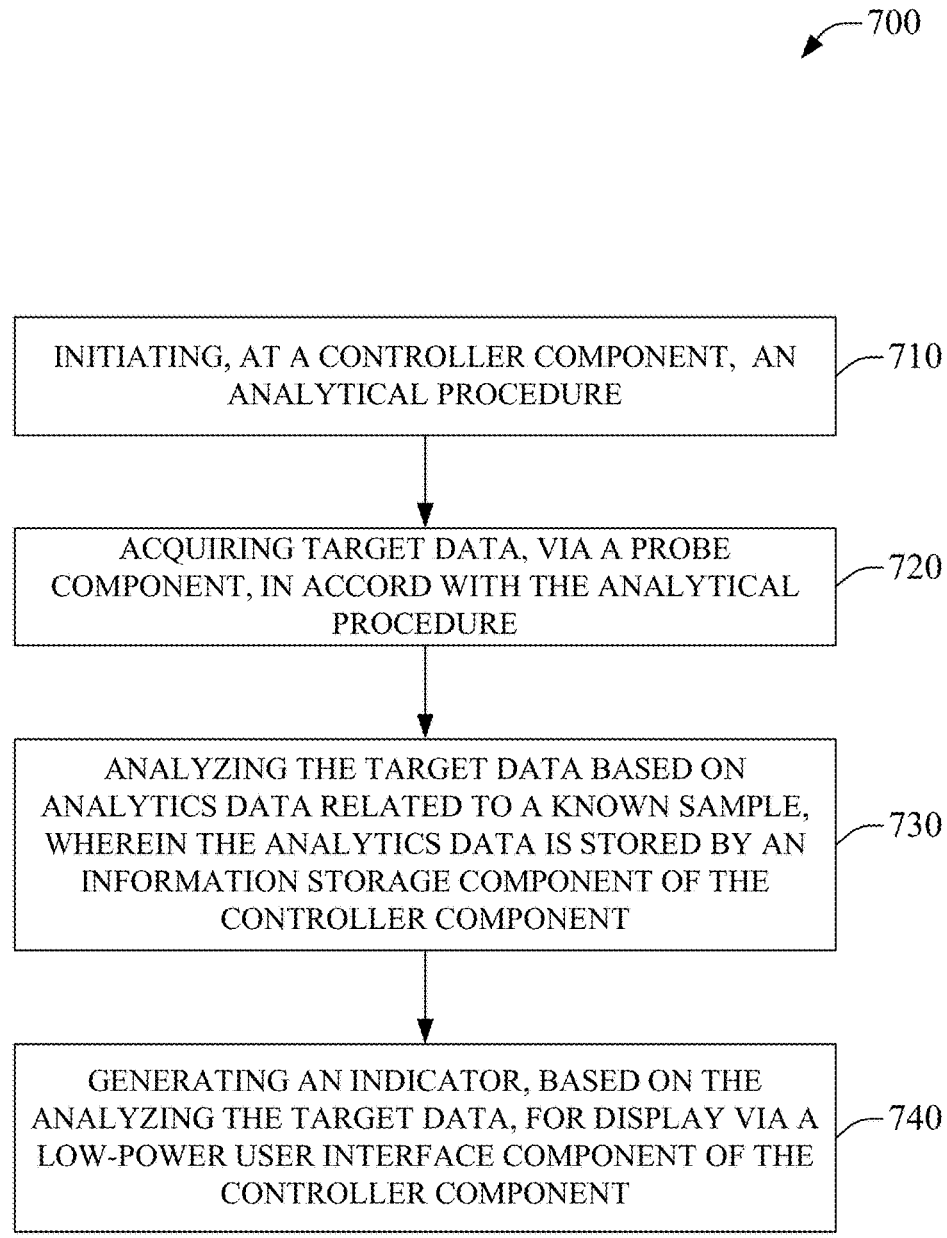
FIG. 7 depicts an example method facilitating portable analytical equipment comprising a low-power user interface feature in accordance with aspects of the subject disclosure.
Figure 8:
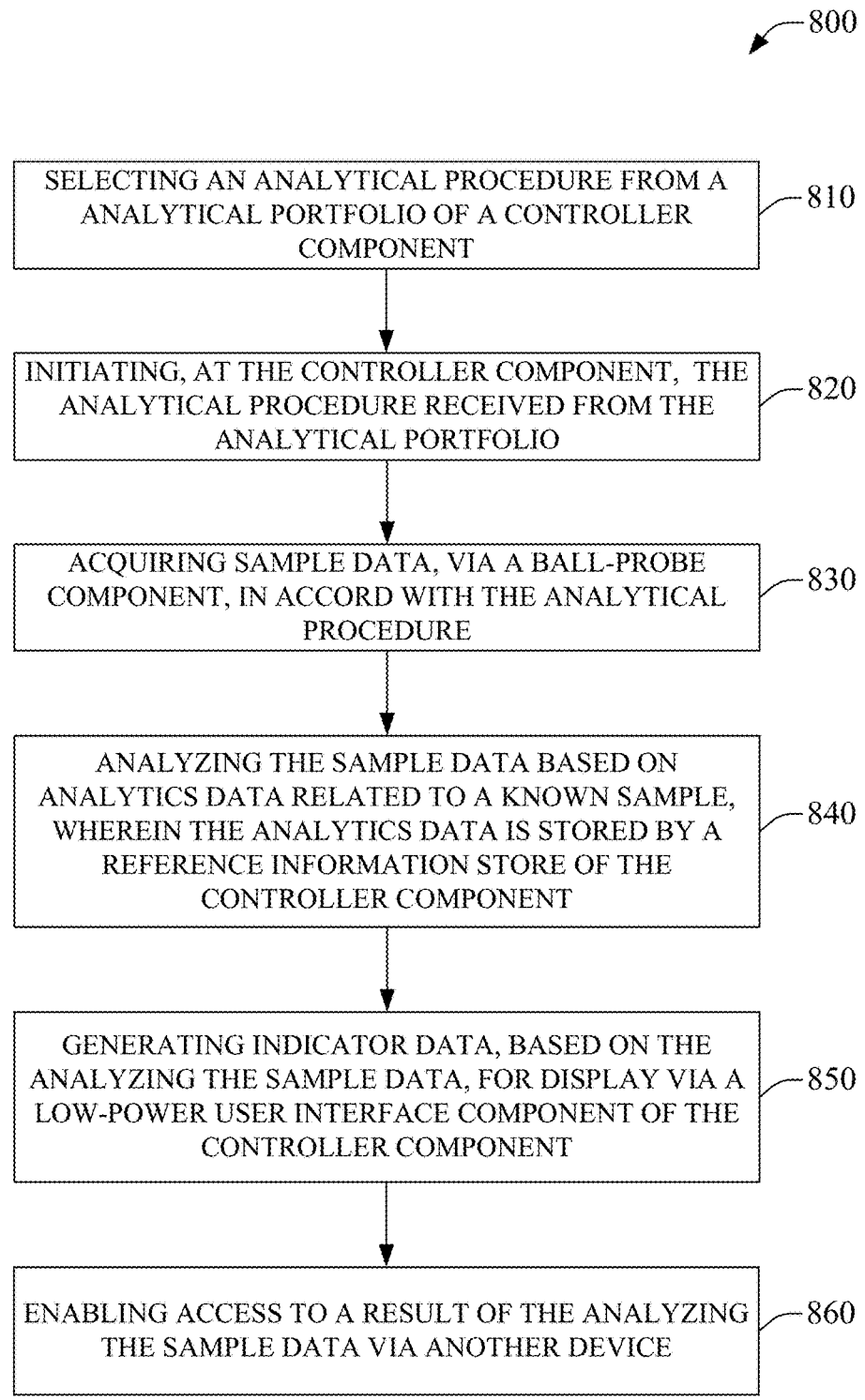
FIG. 8 illustrates an example method facilitating portable analytical equipment, enabling external access to sample data by another device, comprising an on-board analytical portfolio, on-board reference information, and a low-power user interface feature in accordance with aspects of the subject disclosure.
Figure 9:
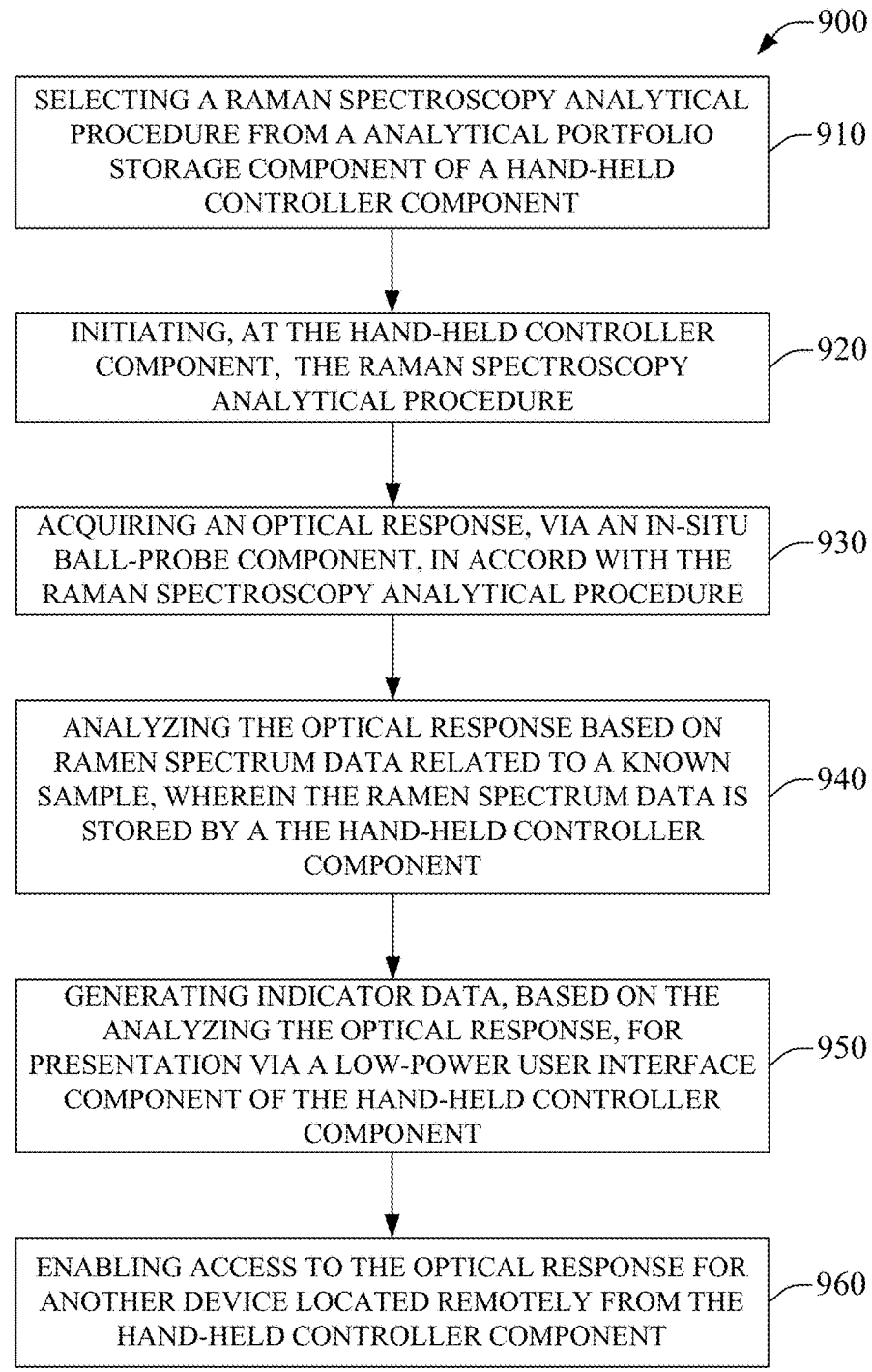
FIG. 9 illustrates an example method facilitating Ramen spectrometry, via a ball-probe component, by a hand-held device that enables access to an optical response by a remotely located device in accordance with aspects of the subject disclosure.

In view of the example system(s) described above, example method(s) that can be implemented in accordance with the disclosed subject matter can be better appreciated with reference to flowcharts in FIG. 7-FIG. 9. For purposes of simplicity of explanation, example methods disclosed herein are presented and described as a series of acts; however, it is to be understood and appreciated that the claimed subject matter is not limited by the order of acts, as some acts may occur in different orders and/or concurrently with other acts from that shown and described herein. For example, one or more example methods disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a described example method in accordance with the subject specification. Further yet, two or more of the disclosed example methods can be implemented in combination with each other, to accomplish one or more aspects herein described. It should be further appreciated that the example methods disclosed throughout the subject specification are capable of being stored on an article of manufacture (e.g., a computer-readable medium) to allow transporting and transferring such methods to computers for execution, and thus implementation, by a processor or for storage in a memory.

FIG. 7 illustrates a method 700 facilitating portable analytical equipment comprising a low-power user interface feature in accordance with aspects of the subject disclosure. At 710, method 700 can comprise initiating, at a controller component, an analytical procedure. The analytical procedure can be received from another device, locally or remotely located, and/or from a memory or storage device of the controller component. The analytical procedure can be stored in a portfolio of analytical procedures. The analytical procedure can be selected based on manual selection or automatic selection related to an environment related to the controller component, e.g., sampling environment (changes in sampling environment, temperature, flow rate, detection of a molecule, concentration/molarity/molality, resistance, viscosity, conductivity, pH, etc.), controller physical environment (temperature, humidity, time, light levels, etc.), etc.

In an aspect, initiation of the analytical procedure can be based on determined parameters and inputs, e.g., inputs from a local or remote user. The parameters can be related to operational conditions, environments, schedules, historical results, historical operations, etc. As an example, an analysis can be initiated based on a determined location in a facility, a schedule, an interval, an elapsed time, etc. Parametric selection and/or rules-based selection or initiation of an analysis can enable device operation without an operator needing to manually select an analysis because where the controller component can determine which analysis should be selected/initiated based on the parameter values and/or rules related to selection of an analysis. Moreover, an analysis can be selected/initiated with, or without, wired or wireless connectivity. In embodiments where a portfolio of analyses is stored on an external storage device, connected to the controller component, an analysis can be initiated/selected therefrom. In additional embodiments, the portfolio of analyses can be stored on another device, e.g., a smart-phone, laptop, tablet computer, etc., or a remotely located device, server, remotely located computer, etc., allowing, initiating/selecting of an analysis from nearly any source.

At 720, target data can be acquired in accord with the analytical procedure initiated at 710. In an aspect, the target data can be acquired via a probe component communicatively coupled to the controller component. In some embodiments, a probe component can be part of, or integrated with, controller component, e.g., the probe can be mechanically attached to a housing that houses a controller component to form a portable analytical equipment device, see for example the example portable analytical equipment device depicted in image 301 of FIG. 3. In an aspect, a probe component can be retractable, in whole or in part. In other embodiments, a probe component can be flexibly connected to a controller component. In an embodiment, the probe component can comprise a BallProbe™ (MarqMetrix Inc., Seattle, Wash.). Ball Probe™ can enable Raman spectrometry of an environment. In an aspect, the BallProbe™ can allow for in-situ Raman spectrometry via the probe component. The BallProbe™ can be controlled by the controller component via a communicative coupling between the controller component and the probe component.

At 730, the target data can be analyzed. The analysis can be based on analytics data related to a known sample. The analytics data can be stored by an information storage component of the controller component. Storage of the analytics data can be part of a library of analytical data to enable performing an analysis based on analytics data stored in the library of analytics data. Analytics data can be received by a controller component from the library. As an example, Raman spectra for known chemical compounds, e.g., a Raman spectral library, can be stored on a memory of a portable analytical equipment device comprising a controller component. The results of a Raman interrogation of a sample can be compared to the Raman spectral library to facilitate analysis of the results of the Raman interrogation. In an aspect, stored analytical data can be tailored to particular applications and can comprise analytical data for known samples of interest in a particular application.

At 740, an indicator can be generated based on the analyzing the target data. At this point method 700 can end. The indicator can be for display via a low-power user interface component of the controller component. A low-power user interface component can display an indicator to allow a user/operator to operate a device meaningfully and with little training. In contrast to an integrated LCD display, which can need skilled interpretation, displaying an indicator can communicate basic, but still meaningful information, to an operator, even those with low skill levels. An operator can therefore be aware of an analysis result and can then determine any need for further testing, a need to have results reviewed by a more highly trained operator, etc.

FIG. 8 illustrates a method 800 that facilitates portable analytical equipment, enabling external access to sample data by another device, comprising an on-board analytical portfolio, on-board reference information, and a low-power user interface feature in accordance with aspects of the subject disclosure. At 810, method 800 can comprise selecting an analytical procedure from an analytical portfolio of a controller component. The analytical procedure can be received from another device, locally or remotely located, and/or from a memory or storage device of the controller component. The analytical procedure can be stored in a portfolio of analytical procedures. The analytical procedure can be selected based on manual selection or automatic selection related to an environment related to the controller component, e.g., sampling environment (changes in sampling environment, temperature, flow rate, detection of a molecule, concentration/molarity/molality, resistance, viscosity, conductivity, pH, etc.), controller physical environment (temperature, humidity, time, light levels, etc.), etc.

At 820, method 800 can comprise initiating, at the controller component, the selected analytical procedure. In an aspect, initiation of the analytical procedure can be based on determined parameters and inputs, e.g., inputs from a local or remote user. The parameters can be related to operational conditions, environments, schedules, historical results, historical operations, etc. As an example, an analysis can be initiated based on a determined location in a facility, a schedule, an interval, an elapsed time, etc. Parametric selection and/or rules-based initiation of an analysis can enable device operation without an operator needing to manually initiate an analysis because the controller component can determine initiation of the selected analysis based on the parameter values and/or rules related to the analysis. Moreover, an analysis can be initiated with, or without, wired or wireless connectivity.

At 830, sample data can be acquired via a BallProbe™ (MarqMetrix Inc., Seattle, Wash.) in accord with the analytical procedure initiated at 820. In an aspect, the target data can be acquired via the BallProbe™ that is communicatively coupled to a controller component. In some embodiments, the BallProbe™ can be part of, or integrated with, controller component, e.g., the BallProbe™ can be mechanically attached to a housing that houses a controller component to form a portable analytical equipment device, see for example the example portable analytical equipment device depicted in image 301 of FIG. 3. In an aspect, the BallProbe™ can be retractable, in whole or in part. In other embodiments, the BallProbe™ can be flexibly connected to a controller component. The BallProbe™ can enable Raman spectrometry of an environment. In an aspect, the BallProbe™ can allow for in-situ Raman spectrometry. The BallProbe™ can be controlled by the controller component via a communicative coupling between the controller component and the probe component.

At 840, the sample data can be analyzed. The analysis can be based on analytics data related to a known sample. The analytics data can be stored in a reference information store of the controller component. Storage of the analytics data can be part of a library of analytic data to enable performing an analysis based on analytics data stored in the library. Analytics data can be received by a controller component from the reference information store. As an example, Raman spectra for known chemical compounds, e.g., a Raman spectral library, can be stored in a reference information store of a memory of a portable analytical equipment device comprising a controller component. The results of a Raman interrogation of a sample can be compared to the Raman spectral library from the reference information store to facilitate analysis of the results of the Raman interrogation.

At 850, an indicator can be generated based on the analyzing the sample data. The indicator can be for display via a low-power user interface component of the controller component. A low-power user interface component can display an indicator to allow a user/operator to operate a device meaningfully and with little training. In contrast to an integrated LCD display, which can need skilled interpretation, displaying an indicator can communicate basic, but still meaningful information, to an operator, even those with low skill levels. An operator can therefore be aware of an analysis result and can then determine any need for further testing, a need to have results reviewed by a more highly trained operator, etc.

At 860, access to a result of the analyzing the sample data can be enabled. At this point, method 800 can end. Access can be for another device. Further, the result of the analyzing can comprise detailed analytical data, more complex than might be communicated via a low-power user interface component. In an embodiment, the controller component can be communicatively coupled with the other device, e.g., a laptop, smartphone, tablet, etc., to allow interaction with the controller component via the other device. The other coupled device can provide a display for visualizing and/or interacting with analytical results that would be generally comparable to, or better than, conventional portable analytical equipment with an embedded display, e.g., coupling to a smartphone can provide similar display area and resolution as conventional portable analytical equipment, and coupling to a tablet or laptop can provide a display that is frequently larger and/or better resolution that displays comprised in conventional portable analytical equipment. Additionally, the increasing performance of these other devices can allow the presently disclosed portable analytical equipment to remain highly relevant where external devices continue to evolve. This can be a considerable advantage over conventional portable analytical equipment because these improving technologies can then be leveraged to provide an improved user experience as they come to market.

FIG. 9 illustrates a method 900 that facilitates Raman spectrometry, via a ball-probe component, by a hand-held device that enables access to an optical response by a remotely located device in accordance with aspects of the subject disclosure. At 910, method 900 can comprise selecting a Raman spectrometry analytical procedure from an analytical portfolio of a controller component embodied in a hand-held device. The Raman spectrometry analytical procedure can be received from another device, locally or remotely located, and/or from a memory or storage device of the controller component. The Raman spectrometry analytical procedure can be stored in a portfolio of analytical procedures. The Raman spectrometry analytical procedure can be selected based on manual selection or automatic selection related to an environment related to the controller component, e.g., sampling environment (changes in sampling environment, temperature, flow rate, detection of a molecule, concentration/molarity/molality, resistance, viscosity, conductivity, pH, etc.), controller physical environment (temperature, humidity, time, light levels, etc.), etc.

At 920, method 900 can comprise initiating, at the controller component, the selected Raman spectrometry analytical procedure. In an aspect, initiation of the Raman spectrometry analytical procedure can be based on determined parameters and inputs, e.g., inputs from a local or remote user. The parameters can be related to operational conditions, environments, schedules, historical results, historical operations, etc. As an example, a Raman spectrometry analysis can be initiated based on a determined location in a facility, a schedule, an interval, an elapsed time, etc. Parametric selection and/or rules-based initiation of an analysis can enable device operation without manual initiation of the Raman spectrometry analysis because the controller component can determine initiation of the selected Raman spectrometry analysis based on the parameter values and/or rules related to the analysis. Moreover, the Raman spectrometry analysis can be initiated with, or without, wired or wireless connectivity.

At 930, an optical response can be acquired in-situ via a BallProbe™ (MarqMetrix Inc., Seattle, Wash.) in accord with the Raman spectrometry analytical procedure initiated at 920. In an aspect, the optical response can be acquired via the BallProbe™ that is communicatively coupled to a controller component. In some embodiments, the BallProbe™ can be part of, or integrated with, controller component, e.g., the BallProbe™ can be mechanically attached to a housing that houses a controller component to form a portable analytical equipment device, see for example the example portable analytical equipment device depicted in image 301 of FIG. 3. In an aspect, the BallProbe™ can be retractable, in whole or in part. In other embodiments, the BallProbe™ can be flexibly connected to a controller component. The BallProbe™ can enable Raman spectrometry of an environment. In an aspect, the BallProbe™ can allow for in-situ Raman spectrometry. The BallProbe™ can be controlled by the controller component via a communicative coupling between the controller component and the probe component.

At 940, the optical response can be analyzed. The analysis can be based on Raman spectrum data related to a known sample. The Raman spectrum data can be stored in a reference information store of the hand held device. Storage of the Raman spectrum data can be part of a library of analytic data to enable performing an analysis based on Raman spectrum data stored in the library. Raman spectrum data can be received by a controller component from the reference information store. The results of a Raman interrogation of a sample can be compared to the Raman spectral library from the reference information store to facilitate analysis of the results of the Raman interrogation.

At 950, an indicator can be generated based on the analyzing the optical response. The indicator can be for display via a low-power user interface component of the hand held device comprising the controller component. A low-power user interface component can display an indicator to allow a user/operator to operate the hand held device meaningfully and with little training. In contrast to an integrated LCD display, which can need skilled interpretation, displaying an indicator can communicate basic, but still meaningful information, to an operator, even those with low skill levels. An operator can therefore be aware of an analysis result and can then determine any need for further testing, a need to have results reviewed by a more highly trained operator, etc.

At 960, access to a result of the analyzing the optical response can be enabled. At this point, method 900 can end. Access can be for another device. The result of the analyzing can comprise detailed analytical data, more complex than might be communicated via a low-power user interface component. In an embodiment, the controller component can be communicatively coupled with the other device, e.g., a laptop, smartphone, tablet, etc., to allow interaction with the controller component via the other device. The other device can provide a display for visualizing and/or interacting with analytical results that would be generally comparable to, or better than, conventional portable analytical equipment with an embedded display, e.g., coupling to a smartphone can provide similar display area and resolution as conventional portable analytical equipment, and coupling to a tablet or laptop can provide a display that is frequently larger and/or better resolution that displays comprised in conventional portable analytical equipment. Additionally, the increasing performance of these other devices can allow the presently disclosed portable analytical equipment to remain highly relevant where external devices continue to evolve. This can be a considerable advantage over conventional portable analytical equipment because these improving technologies can then be leveraged to provide an improved user experience as they come to market.

Figure 10:
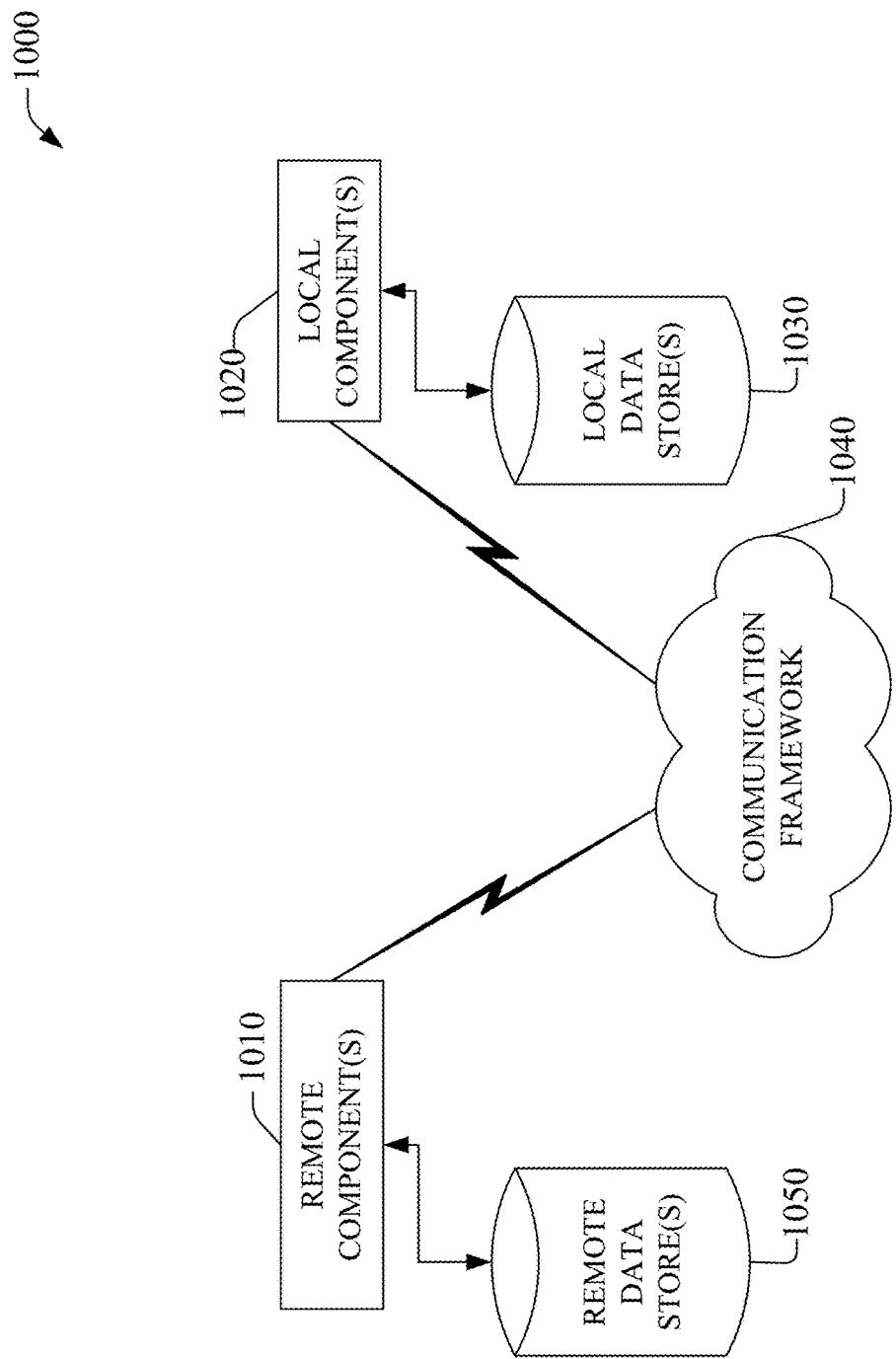
FIG. 10 depicts an example schematic block diagram of a computing environment with which the disclosed subject matter can interact.

FIG. 10 is a schematic block diagram of a computing environment 1000 with which the disclosed subject matter can interact. The system 1000 comprises one or more remote component(s) 1010. The remote component(s) 1010 can be hardware and/or software (e.g., threads, processes, computing devices). In some embodiments, remote component(s) 1010 can comprise servers, personal servers, etc. As an example, remote component(s) 1010 can be remote interface component 450, UE 440, AP 404, etc.

The system 1000 also comprises one or more local component(s) 1020. The local component(s) 1020 can be hardware and/or software (e.g., threads, processes, computing devices). In some embodiments, local component(s) 1020 can comprise, for example, controller component 110-510, UE 440, etc.

One possible communication between a remote component(s) 1010 and a local component(s) 1020 can be in the form of a data packet adapted to be transmitted between two or more computer processes. Another possible communication between a remote component(s) 1010 and a local component(s) 1020 can be in the form of circuit-switched data adapted to be transmitted between two or more computer processes in radio time slots. The system 1000 comprises a communication framework 1040 that can be employed to facilitate communications between the remote component(s) 1010 and the local component(s) 1020, and can comprise an air interface, e.g., Uu interface of a UMTS network. Remote component(s) 1010 can be operably connected to one or more remote data store(s) 1050, such as a hard drive, SIM card, device memory, etc., that can be employed to store information on the remote component(s) 1010 side of communication framework 1040. Similarly, local component(s) 1020 can be operably connected to one or more local data store(s) 1030, that can be employed to store information on the local component(s) 1020 side of communication framework 1040.

Figure 11:
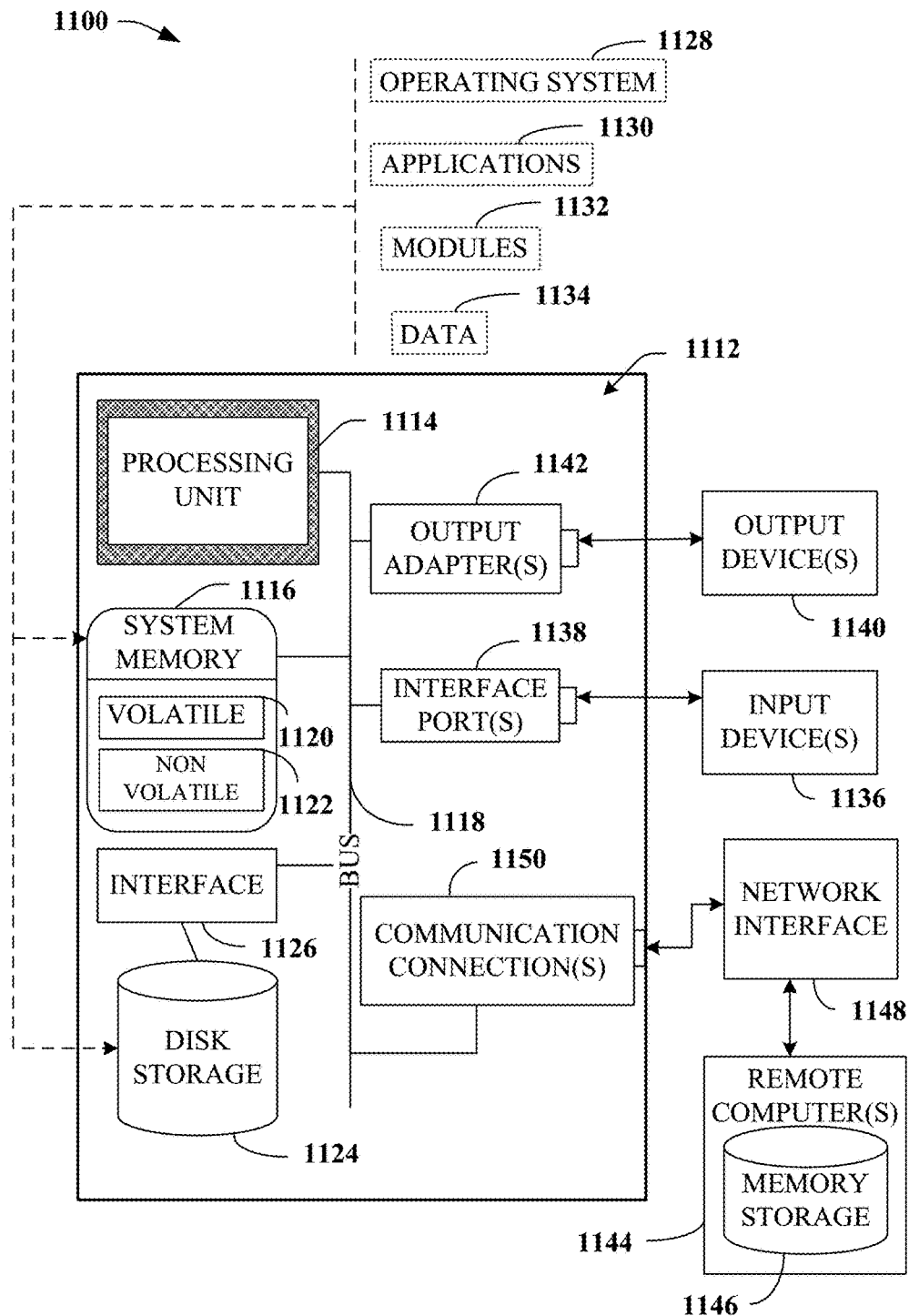
FIG. 11 illustrates an example block diagram of a computing system operable to execute the disclosed systems and methods in accordance with an embodiment.

In order to provide a context for the various aspects of the disclosed subject matter, FIG. 11, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules comprise routines, programs, components, data structures, etc. that performs particular tasks and/or implement particular abstract data types.

In the subject specification, terms such as "store," "storage," "data store," data storage," "database," and substantially any other information storage component relevant to operation and functionality of a component, refer to "memory components," or entities embodied in a "memory" or components comprising the memory. It is noted that the memory components described herein can be either volatile memory or nonvolatile memory, or can comprise both volatile and nonvolatile memory, by way of illustration, and not limitation, volatile memory 1120 (see below), nonvolatile memory 1122 (see below), disk storage 1124 (see below), and memory storage 1146 (see below). Further, nonvolatile memory can be included in read only memory, programmable read only memory, electrically programmable read only memory, electrically erasable read only memory, or flash memory. Volatile memory can comprise random access memory, which acts as external cache memory. By way of illustration and not limitation, random access memory is available in many forms such as synchronous random access memory, dynamic random access memory, synchronous dynamic random access memory, double data rate synchronous dynamic random access memory, enhanced synchronous dynamic random access memory, Synchlink dynamic random access memory, and direct Rambus random access memory. Additionally, the disclosed memory components of systems or methods herein are intended to comprise, without being limited to comprising, these and any other suitable types of memory.

Moreover, it is noted that the disclosed subject matter can be practiced with other computer system configurations, comprising single-processor or multiprocessor computer systems, mini-computing devices, mainframe computers, as well as personal computers, hand-held computing devices (e.g., personal digital assistant, phone, watch, tablet computers, netbook computers, . . . ), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

FIG. 11 illustrates a block diagram of a computing system 1100 operable to execute the disclosed systems and methods in accordance with an embodiment. Computer 1112, which can be, for example, comprised in controller component 110-510, etc., UE 440, AP 404, remote interface component 450, etc., comprises a processing unit 1114, a system memory 1116, and a system bus 1118. System bus 1118 couples system components comprising, but not limited to, system memory 1116 to processing unit 1114. Processing unit 1114 can be any of various available processors. Dual microprocessors and other multiprocessor architectures also can be employed as processing unit 1114.

System bus 1118 can be any of several types of bus structure(s) comprising a memory bus or a memory controller, a peripheral bus or an external bus, and/or a local bus using any variety of available bus architectures comprising, but not limited to, industrial standard architecture, micro-channel architecture, extended industrial standard architecture, intelligent drive electronics, video electronics standards association local bus, peripheral component interconnect, card bus, universal serial bus, advanced graphics port, personal computer memory card international association bus, Firewire (Institute of Electrical and Electronics Engineers 1194), and small computer systems interface.

System memory 1116 can comprise volatile memory 1120 and nonvolatile memory 1122. A basic input/output system, containing routines to transfer information between elements within computer 1112, such as during start-up, can be stored in nonvolatile memory 1122. By way of illustration, and not limitation, nonvolatile memory 1122 can comprise read only memory, programmable read only memory, electrically programmable read only memory, electrically erasable read only memory, or flash memory. Volatile memory 1120 comprises read only memory, which acts as external cache memory. By way of illustration and not limitation, read only memory is available in many forms such as synchronous random access memory, dynamic read only memory, synchronous dynamic read only memory, double data rate synchronous dynamic read only memory, enhanced synchronous dynamic read only memory, Synchlink dynamic read only memory, Rambus direct read only memory, direct Rambus dynamic read only memory, and Rambus dynamic read only memory.

Computer 1112 can also comprise removable/non-removable, volatile/non-volatile computer storage media. FIG. 11 illustrates, for example, disk storage 1124. Disk storage 1124 comprises, but is not limited to, devices like a magnetic disk drive, floppy disk drive, tape drive, flash memory card, or memory stick. In addition, disk storage 1124 can comprise storage media separately or in combination with other storage media comprising, but not limited to, an optical disk drive such as a compact disk read only memory device, compact disk recordable drive, compact disk rewritable drive or a digital versatile disk read only memory. To facilitate connection of the disk storage devices 1124 to system bus 1118, a removable or non-removable interface is typically used, such as interface 1126.

Computing devices typically comprise a variety of media, which can comprise computer-readable storage media or communications media, which two terms are used herein differently from one another as follows.

Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can comprise, but are not limited to, read only memory, programmable read only memory, electrically programmable read only memory, electrically erasable read only memory, flash memory or other memory technology, compact disk read only memory, digital versatile disk or other optical disk storage, magnetic cassettes, magnetic tape, magnetic disk storage or other magnetic storage devices, or other tangible media which can be used to store desired information. In this regard, the term "tangible" herein as may be applied to storage, memory or computer-readable media, is to be understood to exclude only propagating intangible signals per se as a modifier and does not relinquish coverage of all standard storage, memory or computer-readable media that are not only propagating intangible signals per se. In an aspect, tangible media can comprise non-transitory media wherein the term "non-transitory" herein as may be applied to storage, memory or computer-readable media, is to be understood to exclude only propagating transitory signals per se as a modifier and does not relinquish coverage of all standard storage, memory or computer-readable media that are not only propagating transitory signals per se. Computer-readable storage media can be accessed by one or more local or remote computing devices, e.g., via access requests, queries or other data retrieval protocols, for a variety of operations with respect to the information stored by the medium. As such, for example, a computer-readable medium can comprise executable instructions stored thereon that, in response to execution, cause a system comprising a processor to perform operations, comprising: initiating an analysis by controller component 110-510, by aspect 710, 820, 920, etc., and in response, generating information related thereto that can be accessed via a low power interface, e.g., 660A-D, etc., or via a wireless interface by one or more other device, e.g., UE 440, etc.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

It can be noted that FIG. 11 describes software that acts as an intermediary between users and computer resources described in suitable operating environment 1100. Such software can comprise an operating system 1128. Operating system 1128, which can be stored on disk storage 1124, acts to control and allocate resources of computer system 1112. System applications 1130 take advantage of the management of resources by operating system 1128 through program modules 1132 and program data 1134 stored either in system memory 1116 or on disk storage 1124. It is to be noted that the disclosed subject matter can be implemented with various operating systems or combinations of operating systems.

A user can enter commands or information into computer 1112 through input device(s) 1136. In some embodiments, a user interface can allow entry of user preference information, etc., and can be embodied in a touch sensitive display panel, a mouse input GUI, a command line controlled interface, etc., allowing a user to interact with computer 1112. Input devices 1136 comprise, but are not limited to, a pointing device such as a mouse, trackball, stylus, touch pad, keyboard, microphone, joystick, game pad, satellite dish, scanner, TV tuner card, digital camera, digital video camera, web camera, cell phone, smartphone, tablet computer, etc. These and other input devices connect to processing unit 1114 through system bus 1118 by way of interface port(s) 1138. Interface port(s) 1138 comprise, for example, a serial port, a parallel port, a game port, a universal serial bus, an infrared port, a Bluetooth port, an IP port, or a logical port associated with a wireless service, etc. Output device(s) 1140 use some of the same type of ports as input device(s) 1136.

Thus, for example, a universal serial busport can be used to provide input to computer 1112 and to output information from computer 1112 to an output device 1140. Output adapter 1142 is provided to illustrate that there are some output devices 1140 like monitors, speakers, and printers, among other output devices 1140, which use special adapters. Output adapters 1142 comprise, by way of illustration and not limitation, video and sound cards that provide means of connection between output device 1140 and system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. Remote computer(s) 1144 can be a personal computer, a server, a router, a network PC, cloud storage, a cloud service, code executing in a cloud-computing environment, a workstation, a microprocessor based appliance, a peer device, or other common network node and the like, and typically comprises many or all of the elements described relative to computer 1112.

For purposes of brevity, only a memory storage device 1146 is illustrated with remote computer(s) 1144. Remote computer(s) 1144 is logically connected to computer 1112 through a network interface 1148 and then physically connected by way of communication connection 1150. Network interface 1148 encompasses wire and/or wireless communication networks such as local area networks and wide area networks. Local area network technologies comprise fiber distributed data interface, copper distributed data interface, Ethernet, Token Ring, Radius, Diameter, and the like. Wide area network technologies comprise, but are not limited to, point-to-point links, circuit-switching networks like integrated services digital networks and variations thereon, packet switching networks, and digital subscriber lines. As noted below, wireless technologies may be used in addition to or in place of the foregoing.

Communication connection(s) 1150 refer(s) to hardware/software employed to connect network interface 1148 to bus 1118. While communication connection 1150 is shown for illustrative clarity inside computer 1112, it can also be external to computer 1112. The hardware/software for connection to network interface 1148 can comprise, for example, internal and external technologies such as modems, comprising regular telephone grade modems, cable modems and digital subscriber line modems, integrated services digital network adapters, and Ethernet cards.

The above description of illustrated embodiments of the subject disclosure, comprising what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit, a digital signal processor, a field programmable gate array, a programmable logic controller, a complex programmable logic device, a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

As used in this application, the terms "component," "system," "platform," "layer," "selector," "interface," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Further, the term "include" is intended to be employed as an open or inclusive term, rather than a closed or exclusive term. The term "include" can be substituted with the term "comprising" and is to be treated with similar scope, unless otherwise explicitly used otherwise. As an example, "a basket of fruit including an apple" is to be treated with the same breadth of scope as, "a basket of fruit comprising an apple."

Moreover, terms like "user equipment (UE)," "mobile station," "mobile," subscriber station," "subscriber equipment," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "AP," "base station," "Node B," "evolved Node B," "eNodeB," "home Node B," "home access point," and the like, are utilized interchangeably in the subject application, and refer to a wireless network component or appliance that serves and receives data, control, voice, video, sound, gaming, or substantially any data-stream or signaling-stream to and from a set of subscriber stations or provider enabled devices. Data and signaling streams can comprise packetized or frame-based flows.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities or automated components (e.g., supported through artificial intelligence, as through a capacity to make inferences based on complex mathematical formalisms), that can provide simulated vision, sound recognition and so forth.

Aspects, features, or advantages of the subject matter can be exploited in substantially any, or any, wired, broadcast, wireless telecommunication, radio technology or network, or combinations thereof. Non-limiting examples of such technologies or networks comprise broadcast technologies (e.g., sub-Hertz, extremely low frequency, very low frequency, low frequency, medium frequency, high frequency, very high frequency, ultra-high frequency, super-high frequency, terahertz broadcasts, etc.); Ethernet; X.25; power-line-type networking, e.g., Powerline audio video Ethernet, etc.; femtocell technology; Wi-Fi; worldwide interoperability for microwave access; enhanced general packet radio service; third generation partnership project, long term evolution; third generation partnership project universal mobile telecommunications system; third generation partnership project 2, ultra mobile broadband; high speed packet access; high speed downlink packet access; high speed uplink packet access; enhanced data rates for global system for mobile communication evolution radio access network; universal mobile telecommunications system terrestrial radio access network; or long term evolution advanced.

What has been described above includes examples of systems and methods illustrative of the disclosed subject matter. It is, of course, not possible to describe every combination of components or methods herein. One of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A device, comprising:
   a controller portion, comprising:
   a processor; and
   a memory that stores executable instructions that, when executed by the processor, facilitate performance of operations, comprising:
   selecting an analysis profile related to performing an optical interrogation of a sample;
   initiating the optical interrogation based on the analysis profile;
   receiving an optical response to the optical interrogation of the sample;
   in response to analyzing the optical response, determining a result of the optical interrogation of the sample; and
   indicating a condition related to the sample, via a condition indicator portion of the controller portion, based on the result of the optical interrogation of the sample; and
   a probe portion, comprising:
   an optical interface configured to facilitate performance of the optical interrogation of the sample, wherein the sample is in direct contact with a portion of a lensing optical element of the optical interface.

2. The device of claim 1, wherein the condition indicator portion comprises a light emitting diode (LED) for indicating the condition, and wherein the LED is a discrete electrical component.

3. The device of claim 2, wherein the LED emits a first color for indicating a first condition and a second color for indicating a second condition.

4. The device of claim 1, wherein the condition indicator portion comprises a plurality of LEDs, and a combination of emitting and non-emitting LEDs of the plurality of LEDs indicates the condition, and wherein the LEDs of the plurality of LEDs are discrete electrical components.

5. The device of claim 1, wherein the condition indicator portion comprises an electrophoretic element for indicating the condition.

6. The device of claim 1, wherein the selecting the analysis profile is selected from a portfolio of analyses, comprising the analysis profile, stored in the memory of the device to facilitate conducting different optical analyses.

7. The device of claim 6, wherein the analysis profile is updateable in the portfolio of analyses stored in the memory of the device.

8. The device of claim 1, wherein the analyzing the optical response comprises receiving a known optical spectrum.

9. The device of claim 8, wherein the known optical spectrum is stored in the memory of the device.

10. The device of claim 1, wherein the optical interface comprises a spherical or generally spherical lens element at an interface to the sample, and wherein the sample is in direct contact with a portion of the spherical or generally spherical lens element at the interface to the sample.

11. The device of claim 1, wherein the probe portion is at least partially retractable into a handle portion of the device.

12. The device of claim 1, wherein the controller portion communicates the result of the optical interrogation to a user equipment distinct from the device.

13. The device of claim 1, wherein the initiating the optical interrogation of the sample is in response to receiving user input to the device.

14. The device of claim 1, wherein the initiating the optical interrogation of the sample is in response to determining that the condition related to the sample has changed.

15. The device of claim 1, wherein the initiating the optical interrogation of the sample is in response to receiving a trigger signal from another device.

16. The device of claim 1, wherein the optical interrogation comprises Raman spectrometry.

17. A system, comprising:
   a portable optical analysis device, comprising:
   a controller portion that performs an optical interrogation of a sample;
   a result indicator portion that indicates a result of the optical interrogation; and
   a probe portion that in-situ optically interrogates the sample via direct contact between the sample and a lens element of the probe portion; and
   an interface device, distinct from the portable optical analysis device, comprising:
   a display that displays at least a portion of the result of the optical interrogation;
   a user interface that enables modification of a parameter of the portable optical analysis device; and
   a wireless radio that enables communication between the interface device and the portable optical analysis device.

18. The system of claim 17, wherein the portable optical analysis device comprises a memory or a removable storage device communicatively coupled to the controller portion.

19. The system of claim 18, wherein the controller portion of the portable optical analysis device receives information related to one or more reference optical spectra stored on the memory or the removable storage device.

20. The system of claim 18, wherein the controller portion of the portable optical analysis device is configured to access one or more optical analysis profiles stored on the memory or the removable storage device.

21. The system of claim 18, wherein a reference optical spectra or an optical analysis profile stored on the memory or the removable storage device is updated via the interface device.

22. The system of claim 21, wherein the update via the interface device comprises a wireless connection between the portable optical analysis device and the wireless radio of the interface device.

23. The system of claim 21, wherein the update via the interface device comprises a wired connection between the portable optical analysis device and the interface device.

24. The system of claim 17, wherein the result indicator portion comprises at least one LED and the at least one LED enables the portable optical analysis device to indicate a result of the optical interrogation of the sample via a color of an emission from the at least one LED or a pattern of emissions and non-emissions for the at least one LED.

25. A computer readable storage device comprising executable instructions that, in response to execution, cause a system comprising a processor to perform operations, comprising:

selecting an analysis profile related to performing an optical interrogation of a sample via an optical interface configured to perform the optical interrogation of the sample while a lens of the optical interface is in direct contact with the sample;

initiating the optical interrogation based on the analysis profile;

receiving an optical response to the optical interrogation of the sample;

in response to analyzing the optical response, determining a result of the optical interrogation of the sample; and indicating a condition related to the sample, via a condition indicator portion of the controller portion, based on the result of the optical interrogation of the sample.

26. The computer readable storage device of claim 25, wherein the selecting an analysis profile comprises performing the optical interrogation of the sample via an in-situ optical interface.

27. The computer readable storage device of claim 25, wherein the selecting an analysis profile comprises performing the optical interrogation comprising Ramen spectrometry.

28. The computer readable storage device of claim 25, wherein the selecting the analysis profile is selected from a portfolio of analyses, comprising the analysis profile, stored in a memory to facilitate conducting different optical analyses.

* * * * *